(12) United States Patent
Sheehan et al.

(10) Patent No.: US 12,390,450 B2
(45) Date of Patent: Aug. 19, 2025

(54) ANTIPARASITIC POUR-ON COMPOSITIONS

(71) Applicant: Intervet Inc., Madison, NJ (US)

(72) Inventors: John Gerard Sheehan, Nyack, NY (US); Keith Freehauf, Stockton, NJ (US); Annie Flochlay-Sigognault, Angers (FR)

(73) Assignee: Intervet Inc., Rahway, NJ (US)

( * ) Notice: Subject to any disclaimer, the term of this patent is extended or adjusted under 35 U.S.C. 154(b) by 93 days.

(21) Appl. No.: 16/772,576

(22) PCT Filed: Dec. 21, 2018

(86) PCT No.: PCT/EP2018/086558
§ 371 (c)(1),
(2) Date: Jun. 12, 2020

(87) PCT Pub. No.: WO2019/122324
PCT Pub. Date: Jun. 27, 2019

(65) Prior Publication Data
US 2020/0390748 A1 Dec. 17, 2020

Related U.S. Application Data

(60) Provisional application No. 62/608,760, filed on Dec. 21, 2017.

(51) Int. Cl.
| | |
|---|---|
| *A61K 31/42* | (2006.01) |
| *A61K 9/00* | (2006.01) |
| *A61K 9/08* | (2006.01) |
| *A61K 31/05* | (2006.01) |
| *A61K 47/10* | (2017.01) |
| *A61K 47/22* | (2006.01) |
| *A61P 33/14* | (2006.01) |

(52) U.S. Cl.
CPC ............ *A61K 31/42* (2013.01); *A61K 9/0017* (2013.01); *A61K 9/08* (2013.01); *A61K 31/05* (2013.01); *A61K 47/10* (2013.01); *A61K 47/22* (2013.01); *A61P 33/14* (2018.01)

(58) Field of Classification Search
CPC .... A61K 31/42; A61K 31/421; A61K 31/422; A61K 31/423; A61K 31/424; A61K 31/05; A61K 9/0017; A61K 47/22; A61P 33/14

See application file for complete search history.

(56) References Cited

U.S. PATENT DOCUMENTS

| | | | | |
|---|---|---|---|---|
| 2009/0163575 A1* | 6/2009 | Gogolewski | ............ | A61P 33/14 514/603 |
| 2013/0274302 A1 | 10/2013 | Fuchs et al. | | |
| 2013/0281501 A1* | 10/2013 | Fuchs | ................... | A01N 43/80 514/378 |
| 2013/0310372 A1 | 11/2013 | Freehauf et al. | | |
| 2016/0008471 A1* | 1/2016 | Batt | ....................... | A61K 47/14 514/30 |
| 2016/0081986 A1 | 3/2016 | De Rose et al. | | |

FOREIGN PATENT DOCUMENTS

| | | |
|---|---|---|
| AU | 2016202105 B2 | 6/2017 |
| AU | 2016201954 B2 | 11/2017 |
| EP | 2865369 A1 | 4/2015 |
| JP | 2016216489 A | 12/2016 |
| RU | 2481837 C2 | 5/2013 |
| RU | 2633061 C2 | 10/2017 |
| WO | 2005085216 A1 | 9/2005 |
| WO | 2007079162 A1 | 7/2007 |
| WO | 2008122375 A2 | 10/2008 |
| WO | 2009002809 A2 | 12/2008 |
| WO | 2009003075 A1 | 12/2008 |
| WO | 2009024541 A2 | 2/2009 |
| WO | 2009070687 A1 | 6/2009 |
| WO | 2009080250 A2 | 7/2009 |
| WO | 2009156369 A1 | 12/2009 |
| WO | 2010070068 A2 | 6/2010 |
| WO | 2010079077 A1 | 7/2010 |
| WO | 2011075591 A1 | 6/2011 |
| WO | 2011124998 A1 | 10/2011 |
| WO | 2012089622 A2 | 7/2012 |

(Continued)

OTHER PUBLICATIONS

Chen, J., et al., Natural Terpenes as Penetration Enhancers for Transdermal Drug Delivery, Molecules, 2018, pp. 1-22, 21, 1709.

(Continued)

*Primary Examiner* — Michael B. Pallay
(74) *Attorney, Agent, or Firm* — David J. Kerwick

(57) ABSTRACT

Liquid veterinary pour-on or spot-on composition comprising at least one isoxazoline compound of formula (I) and a pharmaceutically acceptable carrier comprising at least one dermal penetration 5 enhancer comprising menthol and a solvent system comprising a pyrrolidone solvent are disclosed. Methods for using and administering such preparation in the prevention and control of parasite infestations in livestock animals are also disclosed.

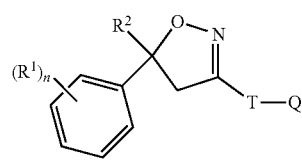

10 Claims, 2 Drawing Sheets

(56) References Cited

FOREIGN PATENT DOCUMENTS

| WO | 2012155352 A1 | 11/2012 |
|---|---|---|
| WO | 2012155676 A1 | 11/2012 |
| WO | 2012158396 A1 | 11/2012 |
| WO | 2013039948 A1 | 3/2013 |
| WO | 2013150055 A1 | 10/2013 |
| WO | 2014039475 A1 | 3/2014 |
| WO | 2015048371 A1 | 4/2015 |
| WO | 2015066277 A1 | 5/2015 |

OTHER PUBLICATIONS

European Search Report for EP18157770.1, dated May 30, 2018, 12 pages.
Holdsworth, P.A. et al, World Association for the Advancement of Veterinary, Veterinary Parasitology, 2006, pp. 29-43, 136, Elsevier.
International Search report for application PCTEP2018086558 mailed on Mar. 27, 2019, 4 sheets.
Khire et al, Bioavailability, bioequivalence, and in vitro-in vivo correlation of oxybutynin transdermal patch in rabbits, Drug Delivery and Translational Research, Aug. 22, 2013, pp. 105-115, vol. 4 No. 2.
Ma et al, effect on ion-pairing on the permeatation of glibenclamide through rat skin, Journal of drug Delivery Science and Technology, Jan. 1, 2008, pp. 279-284, vol. 18 No. 4.
Pfister, K. and Armstrong, R., Systemically and cutaneously distributed ectoparasiticides: a review of the efficacy against ticks and fleas on dogs, Parasites & Vectors, 2016, pp. 1-15, 9:436.
Belikov, V.G., Pharmaceutical Chemistry, Moscow MEDpress-inform, 2007, 27-29, 4th Edition.
Belikov, V.G., Pharmaceutical Chemistry, Moscow MEDpress-inform, 2007, 27-29, 4th Edition—English translation.
Kumar, K. Ajay et al., Isoxazoles: Molecules with potential medicinal properties, IJPCBS, 2013, 294-304, 3(2).
Herman, Anna et al., Essential oils and their constituents as skin penetration enhancer for transdermal drug delivery: a review, Journal of Pharmacy and Pharmacology, 67, 473-485, 2014.

\* cited by examiner

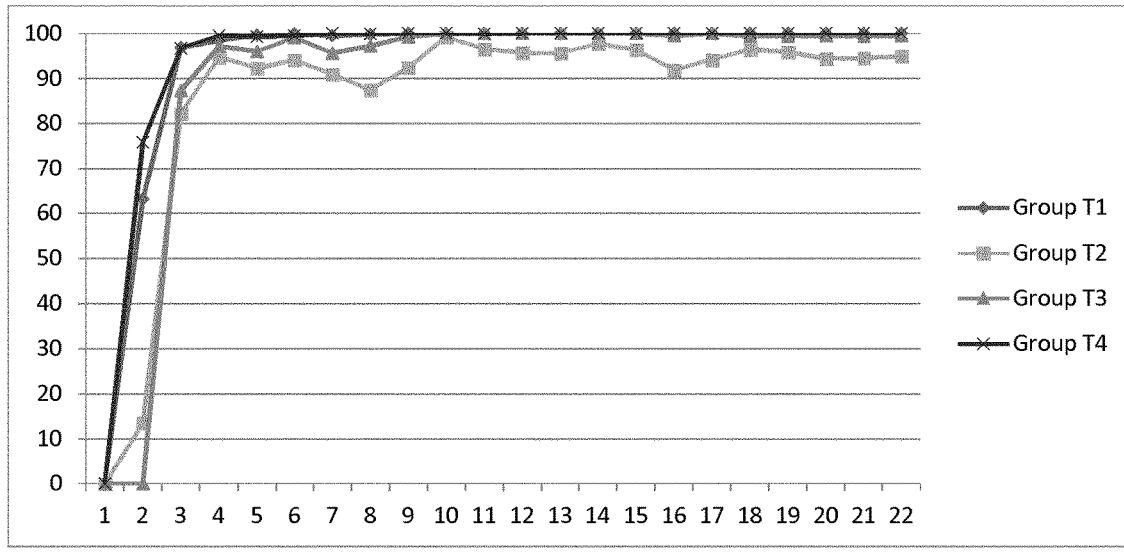
Figure 1 shows the therapeutic efficacy (percent control) of the tested pour-on compositions from Day 1 to day 22
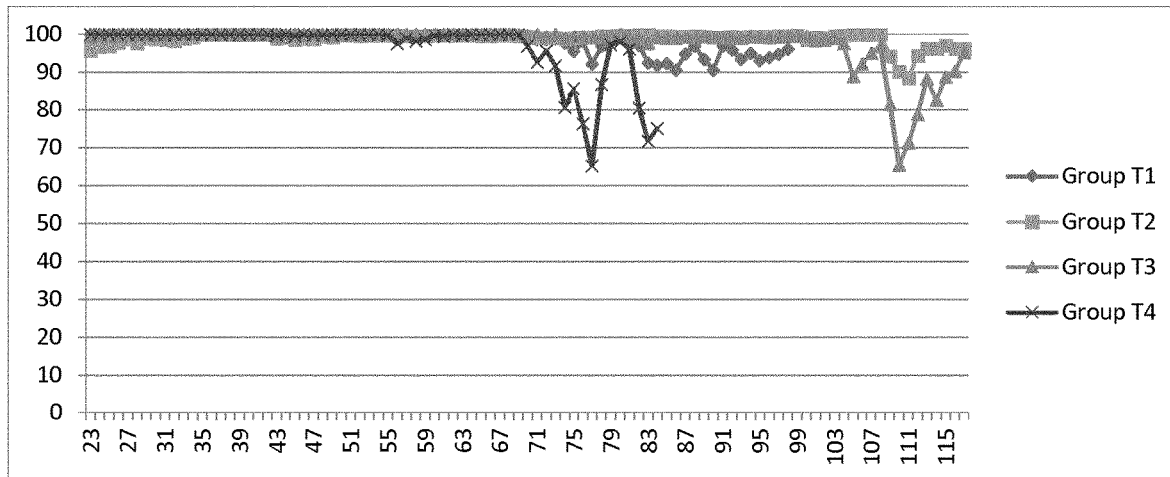
Figure 2 shows the protective efficacy (percent control) of the tested pour-on compositions from Day 23 to day 115

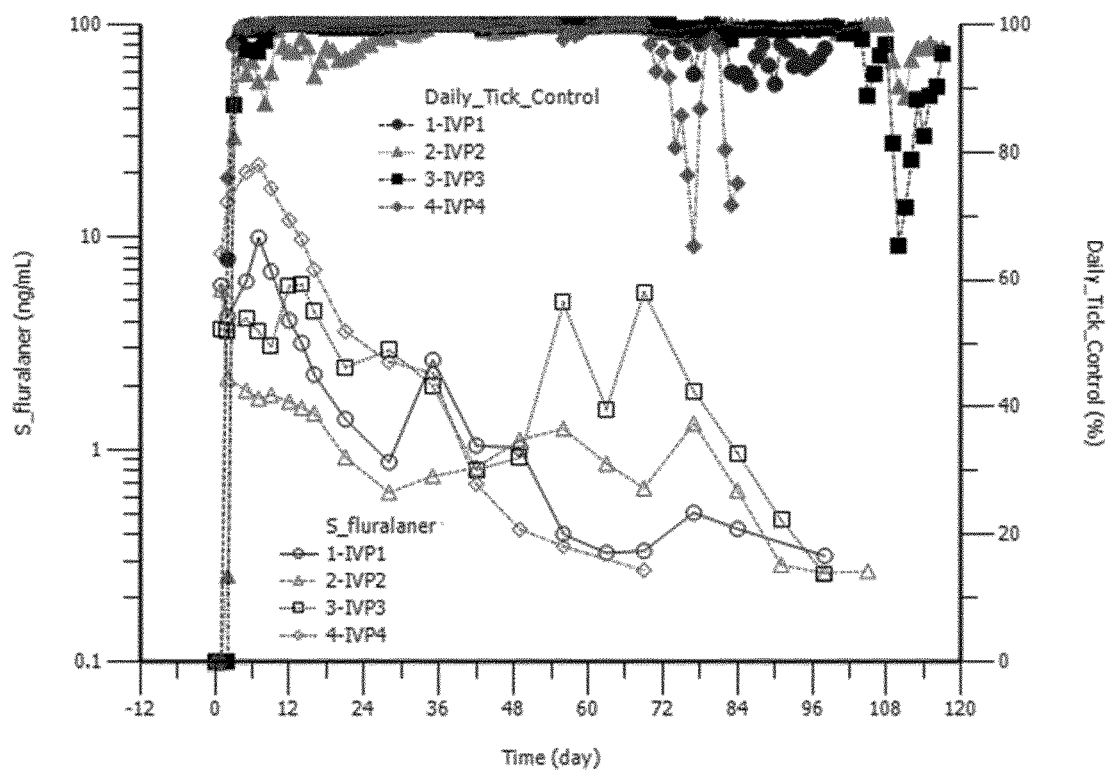
Figure 3 shows the combined tick therapeutic and protective efficacy (Daily tick control %) and the plasma concentration

ANTIPARASITIC POUR-ON COMPOSITIONS

CROSS-REFERENCE TO RELATED APPLICATIONS

This application is a national stage entry under 35 U.S.C. § 371 of PCT/EP2018/086558 filed on Dec. 21, 2018, which claims priority under 35 U.S.C. § 119 (e) of provisional application U.S. Ser. No. 62/608,760 filed Dec. 21, 2017 the contents of which are hereby incorporated by reference in their entireties.

FIELD OF THE INVENTION

The present invention provides veterinary compositions for controlling parasites in animals; the use of these compositions against parasites, and methods for preventing or treating parasitic infections and infestations in animals.

BACKGROUND OF THE INVENTION

Several pests and parasites can infest or infect domestic livestock animals such as cattle, horses, pigs, sheep and also companion animals such as cats and dogs. These pests and parasites are of great nuisance to both the animals and their owners.

Ectoparasites of animals such as ticks, mites, lice, and flies irritate the animals and can cause disease, either by themselves, or by carrying vector transmitted pathogens. Livestock animals such as cattle or sheep are affected by different parasites e.g. by ticks, biting and chewing lice and hematophage biting flies and blowflies.

Especially important ectoparasites of cattle are ticks, e.g. *Rhipicephalus microplus* (cattle tick) and *R. decoloratus* and *R. annulatus*. Infestation by ticks can cause significant economic loss in livestock due to poor quality hide, wool or sheep skin, poor quality meat/tissue, reduced weight gain and reduced milk production.

Furthermore, ticks are additionally responsible worldwide for the transmission and spread of many diseases. They are carriers of bacterial (e.g. Rickettsia), viral and protozoal diseases and cause tick-paralysis and tick-toxicosis.

Sheep and other domesticated livestock are subject to infestation by a wide range of ectoparasites such as lice, blow-fly, ticks, head fly, keds and sheep scab. Of particular importance is the sheep blow fly, such as *Lucilia cuprina, L. serircata, Chrysomyia rufifacies*, and *Calliphora stygia*, whose larvae constitutes a parasite that can cause significant suffering and loss of production in infected sheep. At certain times of the year when blow flies are active, the adult blow fly lays eggs on the sheep. When these eggs hatch the larval stage commences feeding on the flesh of the infected sheep, causing what is known as blow fly strike or sheep myiasis.

The administration of parasiticides to animals, especially to livestock, such as cattle and sheep, is a very labour intensive work and causes stress and loss of body weight to the animals. It requires frequent handling of livestock animals which is undesirable especially in feedlots and on pasture.

Isoxazoline substituted benzamide derivatives are known ectoparasiticides.

Isoxazoline substituted benzamide derivatives were first described in WO 2005/085216 (Nissan Chem. Ind.), as pesticides with potential for veterinary insecticidal- and acaricidal use, and subsequently their use as parasiticides has been further developed.

Meanwhile many variants of isoxazoline pesticides have been described, for example in: WO 2007/079162, WO 2008/122375, WO 2009/002809, WO 2009/024541, WO 2009/080250, WO 2010/070068, WO 2010/079077, WO 2011/075591, WO 2011/124998, WO 2012/155352, WO 2012/155676, WO 2012/158396, WO 2015/048371, WO 2015/066277, and EP 2865369.

Several isoxazoline parasiticides were described specifically for veterinary use in the prevention or treatment of infestations by ectoparasites. Examples are:

Fluralaner (CAS registry number: 864731-61-3), Afoxolaner (CAS RN: 1093861-60-9), Lotilaner (CAS RN: 1369852-71-0), and Sarolaner (CAS RN: 1398609-39-6).

Notwithstanding the compositions comprising isoxazoline active agents alone or in combination with other active agents described in the documents above, there is a need for effective veterinary compositions and methods to protect specifically livestock animals against ectoparasites. Therefore, the invention solves at least one general problem and several specific problems.

Optimal compositions should be efficacious, have a quick onset of activity and a long duration of activity to avoid the necessity of frequent reapplications, and be safe to the host animal and the care takers and have desirable bioavailability and spectrum of coverage too.

Furthermore, optimal composition should be sufficiently easy to apply, and have a limited tendency for wash off during rainfall, retain efficacy on wet animals, dry within a reasonable period of time without impairment of the animal's appearance, be gentle on the animal's coat, have acceptable irritancy to the animal's skin and maintain its effectiveness on the animal through normal activities of the animal, such as exposure to sun and water.

To control external parasites on livestock animals such as sheep, cattle and other animals including goats, pigs, horses and the like, it is a common practice to employ a localized topical application of a pour-on composition containing one or more active ingredients.

Pour-on veterinary compositions of NSAID compounds for the treatment of systemic anti-inflammatory diseases are described in US 2013/0310372.

WO 2012/089622 and WO2013/039948 disclose compositions for topical administration of isoxazoline compounds.

Thus, what is needed in the art, are topical compositions of isoxazoline compounds, which avoid one or more of the drawbacks mentioned above.

SUMMARY OF THE INVENTION

1. The current invention is directed to a liquid veterinary composition for use in the protection and treatment of parasite infestations of animal comprising an effective amount of at least one isoxazoline compound of formula (I)

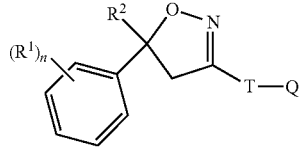

(Formula I)

wherein
R¹=halogen, CF₃, OCF₃, or CN;
n=integer from 0 up to and including 3;
m=1 or 2;
R²=C₁-C₃ haloalkyl;
T=ring structure: 5-, or 6-membered, or bicyclic, which is optionally substituted by one or more radicals Y;
Y=methyl, halomethyl, halogen, CN, NO₂, NH₂—C=S, or two adjacent radicals Y together form a chain;
Q=X—NR³R⁴, NR⁵—NR⁶—X—R³, X—R³, or a 5-membered N-heteroaryl ring, which is optionally substituted by one or more radicals;
X=CH₂, CH(CH₃), CH(CN), CO, CS;
R³=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)carbonylmethyl, propylaminocarbonylmethyl, cyclopropylaminocarbonylmethyl, propenylaminocarbonylmethyl, haloethylaminocarbonylcyclopropyl, alkylsulfanylalkyl, alkylsulfinylalkyl, alkylsulfonylalkyl, cycloalkyl,

R³-1

R³-2

R³-3

R³-4

R³-5

R³-6

R³-7

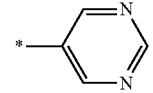
R³-8

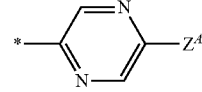
R³-9

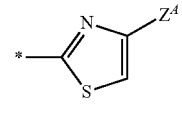
R³-10

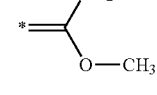
R³-11

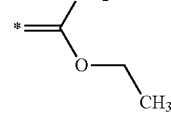
R³-12

R³-13

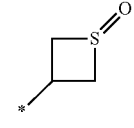
R³-14

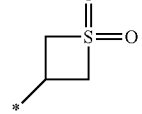
R³-15

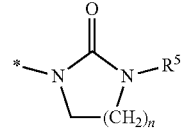
R³-16

R³-17

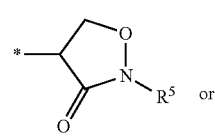
R³-18 wherein
Z^A=hydrogen, halogen, cyano, or halomethyl (CF₃);
R⁴=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;
$R^5$=H, alkyl, or haloalkyl;
$R^6$=H, alkyl, or haloalkyl;
or wherein $R^3$ and $R^4$ together form a substituent selected from the group consisting of:

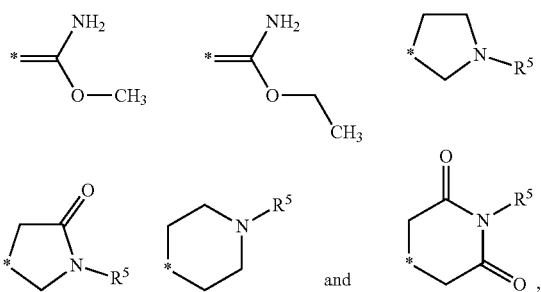

or a pharmaceutically acceptable salt thereof, wherein the composition is administered as a pour on or spot on and comprises a pharmaceutically acceptable carrier comprising at least one dermal penetration enhancer and a solvent system, wherein the dermal penetration enhancer comprises menthol, and the solvent system comprises a pyrrolidone solvent.

In one embodiment the solvent system comprises a volatile solvent.

In another embodiment the composition comprises a glycerol ester.

In one embodiment the composition is administered as a spot-on

In another embodiment the composition is administered as a pour-on.

In one embodiment the invention is a method of protecting a livestock animal, e.g. cattle or sheep animal from ectoparasite infestation comprising administering an effective dose of the liquid veterinary pour-on or spot-on composition as described in this application to an animal in need thereof.

In another embodiment the invention is a method of treating a tick, mite or lice infestation of a cattle animal comprising administering an effective dose of the liquid veterinary pour-on or spot-on composition as described in this application to an animal in need thereof.

In another embodiment the invention is a method of administering a pour-on composition as described in this application for use in the any of the methods described above comprising:
a) Incorporating said composition into a press—in bottle application device; and
b) administering an effective amount of said composition to an animal in need thereof by pour-on administration on the back of the animal.

DESCRIPTION OF THE FIGURES

FIG. 1 shows the therapeutic tick efficacy against (*Rhipicephalus microplus*) in cattle that was obtained when administering the pour-on compositions comprising 5 mg/kg bw of fluralaner to tick infested cattle from Day 1 to day 22 of the study. The graph shows compositions according to the invention No. 72 (T2) and No. 73 (T3) compared to alternative pour-on compositions (Table 4—No 71 (T1) and No. 74 (T4) on day 0

FIG. 2 shows the long-term tick efficacy against (*Rhipicephalus microplus*) in cattle that was obtained when administering the pour-on compositions to tick infested cattle from Day 23 to day 115 of the study.

FIG. 3 illustrates the combination the information about the daily tick control in % from FIGS. 1 and 2 above and the plasma concentration of Fluralaner in the blood in one graph.

DETAILED DESCRIPTION

The present invention provides liquid veterinary compositions comprising at least one isoxazoline compound, alone or in combination with other active agents, and their use to control parasites of livestock animals.

Therefore, it is an object of the invention to provide a method for the prevention, treatment and control of parasite, especially ectoparasitic infection or infestation in a livestock animal, especially cattle and sheep by administration of a pour-on or spot-on composition of the current invention.

An advantageous pour-on or spot-on veterinary application would be one that enables a single administration, to provide efficacious protection of the treated animals over an extended time period preferably over a 21 days period or longer. Besides the duration of effectiveness, the technical features of the pharmaceutical composition, e.g. easiness of application (applicability/viscosity), side effects (local tolerance) and residues in the animal body (especially in livestock) are important features.

In accordance with this invention, it has been discovered that the compositions according to the invention generally show one or more of such beneficial technical features.

In addition, it has been discovered that a single administration of such compositions generally provides potent activity against one or more ectoparasites, while also tending to provide fast onset of activity, long duration of activity, and/or desirable safety profiles toward the host animals and animal care taker.

Such pour-on or spot-on compositions have been surprisingly discovered to be (chemically) stable, i.e. that the active ingredient does not degrade and that there are no incompatibilities caused by the excipients. Furthermore, the compositions are easy to administer to the animals.

The expression pour-on is understood to refer to a ready-to-use concentrate intended to be applied topically and locally on the animal with the assistance of a suitable device such as a measuring cup or squirt bottle or an automatic microspray device.

The pour-on composition is typically applied by pouring in one or several lines or in a spot-on along the dorsal midline (back) or shoulder of an animal. More typically, the composition is applied by pouring it along the back of the animal, following the spine.

Such pour on administration permits directed application of a small amount of composition onto the skin of the animal being treated whereby the active ingredient migrates (spreads) as to protect the whole external surface of the animal and if desired, the active ingredient (depending on the molecule) enters the body through permeation of the skin and acts transdermally. Preferably effective blood levels are obtained by the administration of the composition according to the invention. The cattle skin is known to be especially difficult for transdermal administration. Therefore, it was unexpected to obtain effective blood levels after pour-on or spot-on administration of the composition of the invention. Even more unexpected was the duration of the protection. Therefore, in one embodiment the composition according to the invention is administered to cattle and protects cattle animals from ectoparasites for more than 2 weeks, preferably more than 4 weeks, more preferably more than 6 weeks, 8 weeks, 10 weeks or 12 weeks.

Pour-on compositions can be in the form of a liquid, emulsion, foam, paste, aerosol, ointment, salve or gel. Typical compositions are liquid or semi-liquid dosage forms. Typically, the pour-on composition is a liquid and has a sufficient viscosity that prevents run-off from the animals' fur or skin by sufficient adherence to the fur/skin of the animal after administration but can be easy administered, e.g. expelled the correct amount from the container at various temperatures.

Liquid dosage forms that would be suitable as a pour-on composition are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability.

For successful formulation as a pour-on a compound must be active when dissolved, dispersed or emulsified in a suitable solvent which is well tolerated by the animal's skin.

Preferably for cattle animals a volume of 30 ml and sheep animals 10 ml or less per animal of the pour-on composition is administered. In one embodiment the composition comprises a viscosity increasing component. Pour-on compositions are in one embodiment solutions of the active ingredient. In one embodiment the pour-on solution includes 50% w/v of the active ingredient, the isoxazoline compound, especially fluralaner. In another embodiment the concentration of the active ingredient is between 40 and 50% w/v. In another embodiment the concentration is between 30 and 40%. The composition according to the invention has the benefit that there is no precipitation of the active ingredient and that it results in effective blood levels after spot-on or pour-on administration.

The expression spot-on is understood to refer to a ready-to-use concentrate intended to be applied topically and locally on the animal at a low dose volume with the assistance of a suitable device such as a pipette or a syringe. Alternative a multi-dose applicator is used.

The spot-on composition is typically applied by administering one or several spots along the dorsal midline (back) or shoulder of an animal. More typically, the composition is applied as a spot between the shoulder of the animal. Preferably for sheep animals a volume of 10 ml or less and for cattle 30 ml per animal of the spot-on composition is administered. Spot-on compositions are in one embodiment solutions of the active ingredient. In one embodiment the spot-on solution includes 50% w/v of the active ingredient, the isoxazoline compound, especially fluralaner. In another embodiment the concentration of the active ingredient is between 40 and 50% w/v. In another embodiment the concentration is between 20 and 40%. The composition according to the invention has the benefit that there is no precipitation of the active ingredient and that it results in effective blood—levels after spot-on or pour-on administration.

In an alternative embodiment, especially for sheep a concentration between 1 and 10% w/v of the active ingredient is applied to sheep. Preferably 2-8% w/v, more preferably 2.5 5% w/v.

Such spot-on administration permits directed application of a small amount of composition onto the skin of the animal being treated whereby the active ingredient migrates (spreads), as to protect the whole external surface of the animal and if desired, the active ingredient (depending on the molecule) enters the body through permeation of the skin and acts transdermally.

Spot-on compositions can be in the form of a liquid, emulsion, foam, aerosol, ointment, salve or gel. Typical compositions are liquid or semi-liquid dosage forms. Typically, the spot-on composition is a liquid and has a sufficient viscosity that prevents run-off from the animals' fur or skin by sufficient adherence to the fur/skin of the animal after administration but can be easy administered, e.g. expelled the correct amount from the container at various temperatures.

Liquid dosage forms that would be suitable as a spot-on composition are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability.

For successful formulation as a pour-on or spot-on a compound must be active when dissolved, dispersed or emulsified in a suitable solvent which is well tolerated by the animal's skin.

The compound should be readily absorbable through the animal's skin if transdermal activity is desired and the composition as a whole should disperse or spread well over the animal's body and have a relatively low viscosity when so spread.

It must also be recognized that each compound has its own chemical and physical properties that require special consideration and limit the types of solvents, diluents, stabilizing agents and other excipients that can be used.

One difficulty faced, however, when attempting to arrive at a pour-on transdermal composition is the fact that the skin has been described as a "black box" with regard to drug delivery. This is due to the lack of knowledge in the mechanisms of drug penetration through the epidermis and partitioning into the underlying layers. Thus far, the boundaries for such properties have not been defined; making it very difficult to predict what compounds can be delivered effectively transdermally.

Transdermal systems effective for delivering one compound are almost always ineffective with other compounds. Also, systems and devices that work in one species are usually ineffective in other species. Furthermore, due to the presence of the stratum corneum barrier, the mass transfer through the skin is usually too slow for rapid, massive systemic absorption. This explains why very few, if not any, of the commercially available transdermal products for human use are designed for immediate drug delivery or for long action. Transdermal drugs that work in humans are most of the time not suitable for fur bearing animals, especially for bovine animals such as cattle. The cattle skin has been found to be very challenging for transdermal compositions. Therefore, one embodiment is a pour-on or spot-on composition for cattle.

The compositions according to the invention allow or facilitate the isoxazoline compound to penetrate the skin and act on other body parts (e.g., the entire body). Such a pour-on or spot-on composition can be prepared by dissolving, suspending, or emulsifying the isoxazoline in a suitable veterinarily or pharmaceutically acceptable carrier.

The composition according to the invention avoids the disadvantage to run off wet animals or be washed off by rainfall which occurred after treatment. On contact with water, the active ingredient rapidly precipitates out of prior compositions which are based on water miscible solvents. If this composition is applied to a wet animal, or if the animal is exposed to rain before the treatment has dried on the animal, the active precipitates out of solution and is deposited along the back of the animal, the solvents also being washed away by the rain. This hinders or prevents transdermal absorption, if desired, and the spread of the active ingredient around the entire animal. This phenomenon is particularly important to those areas on the underside of the animal. This may reduce the effectiveness under these conditions.

Realistically the ideal veterinary composition designed for on-farm use on cattle or sheep, especially cattle should have a shelf life of at least 12 months and preferably 24 months at 30° C., with no overage required to attain that shelf life.

"Pharmaceutically or veterinarily acceptable carrier" means a carrier that is useful in preparing a pharmaceutical composition that is generally safe, non-toxic, and neither biologically nor otherwise undesirable, and includes a carrier that is acceptable for veterinary use or pharmaceutical use.

In some embodiments, the topical veterinary composition comprises a pharmaceutically acceptable carrier wherein the carrier comprises at least one solvent and at least one penetration enhancer.

For use in the invention, the 'isoxazoline' or isoxazoline compound is the following compound:

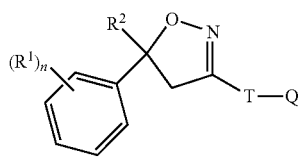

(Formula I)

wherein
$R^1$=halogen, $CF_3$, $OCF_3$, or CN;
n=integer from 0 up to and including 3;
m=1 or 2;
$R^2$=$C_1$-$C_3$ haloalkyl;
T=ring structure: 5-, or 6-membered, or bicyclic, which is optionally substituted by one or more radicals Y;
Y=methyl, halomethyl, halogen, CN, $NO_2$, $NH_2$—C=S, or two adjacent radicals Y together form a chain;
Q=X—$NR^3R^4$, $NR^5$—$NR^6$—X—$R^3$, X—$R^3$, or a 5-membered N-heteroaryl ring, which is optionally substituted by one or more radicals;
X=$CH_2$, $CH(CH_3)$, CH(CN), CO, CS;
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl, alkylsulfanylalkyl, alkylsulfinylalkyl, alkylsulfonylalkyl, cycloalkyl,

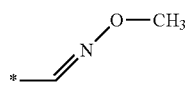

$R^3$-1

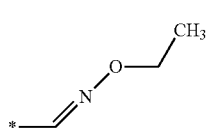

$R^3$-2

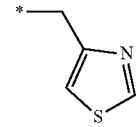

$R^3$-3

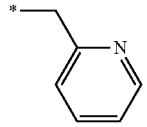

$R^3$-4

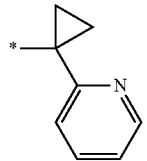

$R^3$-5

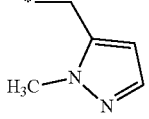

$R^3$-6

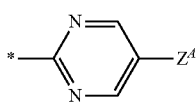

$R^3$-7

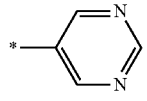

$R^3$-8

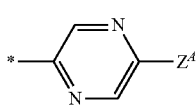

$R^3$-9

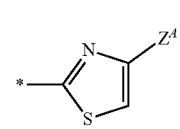

$R^3$-10

-continued

R³-11 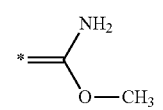

R³-12 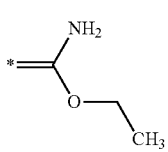

R³-13 

R³-14 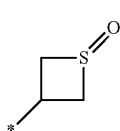

R³-15 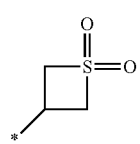

R³-16 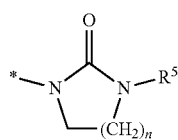

R³-17 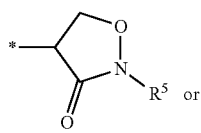

R³-18 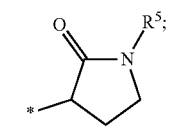

wherein $Z^4$=hydrogen, halogen, cyano, or halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

$R^5$=H, alkyl, or haloalkyl;

$R^6$=H, alkyl, or haloalkyl;

or wherein $R^3$ and $R^4$ together form a substituent selected from the group consisting of:

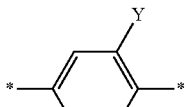

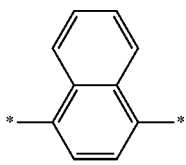

In an embodiment T is selected from

T-1 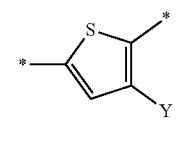

T-2 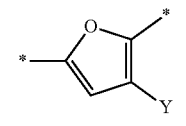

T-3 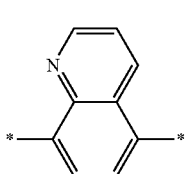

T-4

T-5 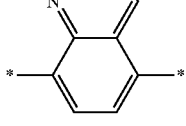

T-6

T-7 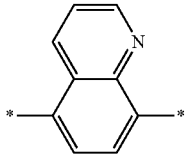

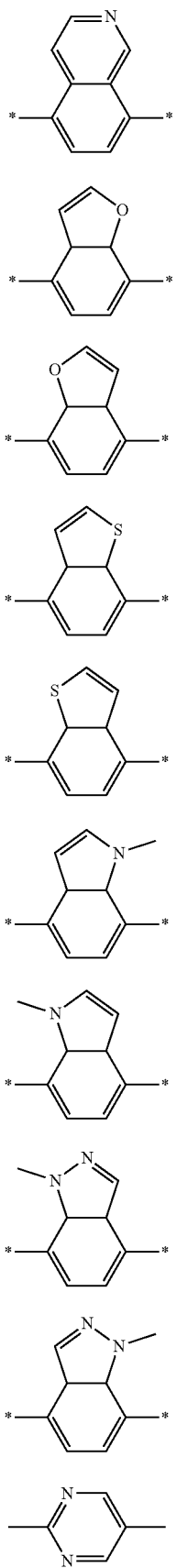
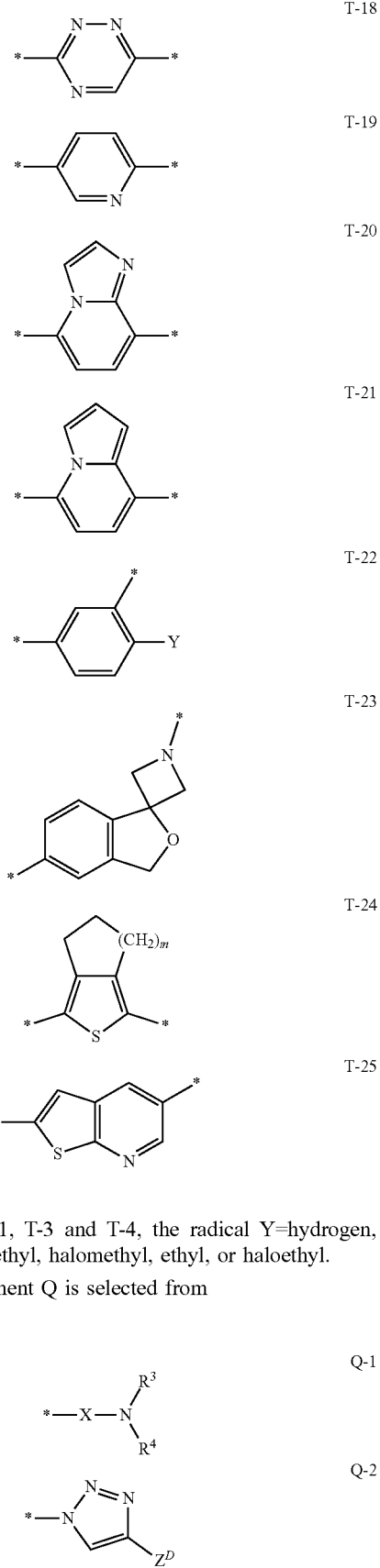
wherein in T-1, T-3 and T-4, the radical Y=hydrogen, halogen, methyl, halomethyl, ethyl, or haloethyl.
In an embodiment Q is selected from
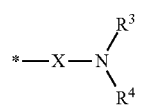
Q-1
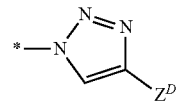
Q-2

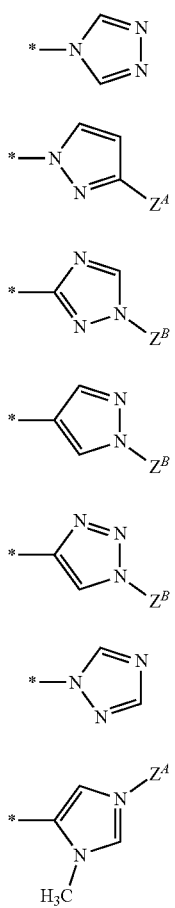
Q-3
Q-4
Q-5
Q-6
Q-7
Q-8
Q-9
wherein $R^3$, $R^4$, X and $Z^A$ are as defined above, and
$Z^B =$
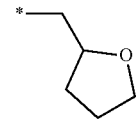 $Z^B$-1
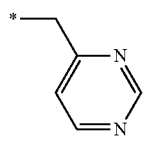 $Z^B$-2
$Z^B$-3
$Z^B$-4
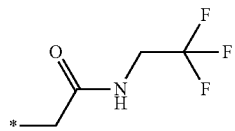 $Z^B$-5
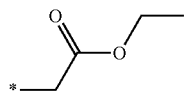 $Z^B$-6
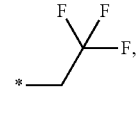 $Z^B$-7
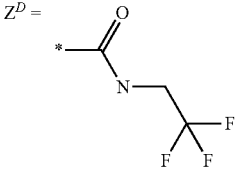 $Z^B$-8
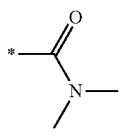 $Z^B$-9
$Z^D =$ 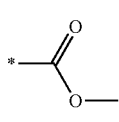 $Z^D$-1
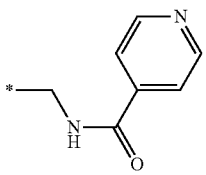 $Z^D$-2
$Z^D$-3
$Z^D$-4
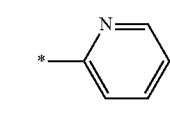 $Z^D$-5
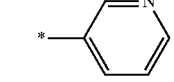 $Z^D$-6
In an embodiment in the isoxazoline of formula (I) $(R_1)_n$, $R_2$, $R_3$, $R_4$, T, Y, Q, Z and X are as presented in Table 1.

TABLE 1

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-Cl, 5-Cl | $CF_3$ | $CH_2C(O)NHCH_2CH_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CH_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CH_3$ | H | T-2 | — | Q-1 | $Z^B$-7 | CO |
| 3-Cl, 5-Cl | $CF_3$ | — | | T-2 | — | Q-6 | $Z^B$-7 | CO |
| 3-Cl, 5-Cl | $CF_3$ | — | — | T-2 | — | Q-7 | $Z^B$-7 | CO |
| 3-Cl, 5-Cl | $CF_3$ | — | — | T-2 | — | Q-5 | $Z^B$-7 | CO |
| 3-Cl, 5-Cl | $CF_3$ | — | — | T-2 | — | Q-2 | $Z^D$-1 | CO |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-Cl, 5-Cl | $CF_3$ | $CH_2C(O)NHCH_2CN$ | H | T-3 | $CH_3$ | Q-1 | — | CO |
| 3-Cl, 5-Cl | $CF_3$ | $CH_2C(O)NHCH_2CH_3$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-$CF_3$, 5-$CF_3$ | $CF_3$ | $CH_2C(O)NHCH_2CH_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CH_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CH_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-Cl, 5-Cl | $CF_3$ | $CH_2C(O)NHCH_2CH_3$ | H | T-20 | — | Q-1 | — | CO |
| 3-$CF_3$, 5-$CF_3$ | $CF_3$ | $CH_2C(O)NHCH_2CF_3$ | $CH_3$ | T-20 | — | Q-1 | — | CO |
| 3-$CF_3$, 5-$CF_3$ | $CF_3$ | $CH_2C(O)NHCH_2CH_3$ | $CH_3$ | T-20 | — | Q-1 | — | CO |
| 3-$CF_3$, 5-$CF_3$ | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CH_3$ | H | T-20 | — | Q-1 | — | CO |
| 3-$CF_3$, 5-$CF_3$ | $CF_3$ | $CH_2C(O)NHCH_2CF_3$ | H | T-21 | — | Q-1 | — | CO |
| 3-$CF_3$, 5-$CF_3$ | $CF_3$ | $CH_2C(O)NHCH_2CH_3$ | H | T-21 | — | Q-1 | — | CO |
| 3-Cl, 5-Cl | $CF_3$ | $CH_2C(O)NHCH_2CF_3$ | H | T-21 | — | Q-1 | — | CO |
| 3-Cl, 5-Cl | $CF_3$ | $CH_2C(O)NHCH_2CH_3$ | H | T-21 | — | Q-1 | — | CO |
| 3-Cl, 5-Cl | $CF_3$ | $CH_2CH_2SCH_3$ | H | T-21 | — | Q-1 | — | CO |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | $C(O)$-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | CO |
| 3-Cl, 5-Cl | $CF_3$ | $CH_2C(O)NHCH_2CH_3$ | H | T-1 | $CH_3$ | Q-1 | — | CO |
| 3-Cl, 5-Cl | $CF_3$ | $R^3$-1 (Z) | H | T-1 | $CH_3$ | Q-1 | — | CO |
| 3-Cl, 5-Cl | $CF_3$ | $R^3$-1 (E) | H | T-1 | $CH_3$ | Q-1 | — | CO |

In an embodiment in the isoxazoline of formula (I) $(R^1)_n$, $R^2$, $R^3$, $R^4$, T, Y, Q, Z and X are as presented in Table 2.

TABLE 2

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-Cl, 5-Cl | $CF_3$ | — | | T-2 | — | Q-6 | $Z^B$-7 | |
| 3-Cl, 5-Cl | $CF_3$ | — | — | T-2 | — | Q-7 | $Z^B$-7 | |
| 3-Cl, 5-Cl | $CF_3$ | — | — | T-2 | — | Q-5 | $Z^B$-7 | |
| 3-Cl, 5-Cl | $CF_3$ | — | — | T-2 | — | Q-2 | $Z^D$-1 | |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-Cl, 5-Cl | $CF_3$ | $CH_2C(O)NHCH_2CN$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CF_3$ | $CH_3$ | T-20 | — | Q-1 | — | CO |
| 3-$CF_3$, 5-$CF_3$ | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CF_3$ | H | T-21 | — | Q-1 | — | CO |
| 3-Cl, 5-Cl | $CF_3$ | $CH_2C(O)NHCH_2CF_3$ | H | T-21 | — | Q-1 | — | CO |
| 3-Cl, 5-Cl | $CF_3$ | $CH_2CH_2SCH_3$ | H | T-21 | — | Q-1 | — | CO |
| 3-Cl, 4-Cl, 5-Cl | $CF_3$ | $C(O)CH_3$ | H | T-22 | F | Q-1 | — | $CH_2$ |

TABLE 2-continued

| (R$^1$)$_n$ | R$^2$ | R$^3$ | R$^4$ | T | Y | Q | Z | X |
|---|---|---|---|---|---|---|---|---|
| 3-Cl, 4-Cl, 5-Cl | CF$_3$ | C(O)CH(CH$_3$)$_2$ | H | T-22 | F | Q-1 | — | CH$_2$ |
| 3-Cl, 4-Cl, 5-Cl | CF$_3$ | C(O)-cyclo-propyl | H | T-22 | F | Q-1 | — | CH$_2$ |
| 3-Cl, 4-F, 5-Cl | CF$_3$ | C(O)CH$_3$ | H | T-22 | F | Q-1 | — | CH$_2$ |
| 3-Cl, 4-Cl, 5-Cl | CF$_3$ | C(O)CH$_2$CH$_3$ | H | T-22 | F | Q-1 | — | CH$_2$ |
| 3-Cl, 4-F, 5-Cl | CF$_3$ | C(O)CH$_3$ | H | T-22 | Cl | Q-1 | — | CH$_2$ |
| 3-Cl, 5-Cl | CF$_3$ | CH$_2$C(O)NHCH$_2$CF$_3$ | H | T-1 | CH$_3$ | Q-1 | — | CO |
| 3-Cl, 5-Cl | CF$_3$ | R$^3$-1 (Z) | H | T-1 | CH$_3$ | Q-1 | — | CO |
| 3-Cl, 5-Cl | CF$_3$ | R$^3$-1 (E) | H | T-1 | CH$_3$ | Q-1 | — | CO |

In an embodiment an isoxazoline for use in the invention is the compound:

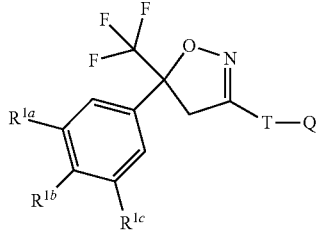

(Formula II)

wherein R$^{1a}$, R$^{1b}$, R$^{1c}$ are independently from each other: hydrogen, Cl or CF$_3$.

Preferably R$^{1a}$ and R$^{1c}$ are Cl or CF$_3$, and R$^{1b}$ is hydrogen, T is

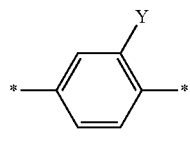 T-1

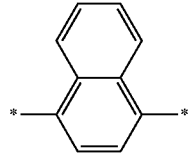 T-2

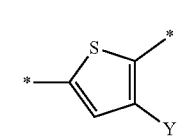 T-3

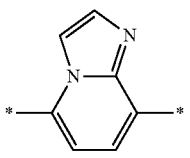 T-20

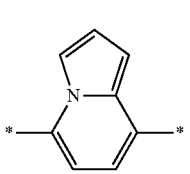 T-21

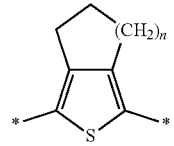 T-23

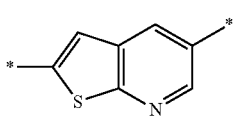 T-24 wherein Y is methyl, bromine, C, F, CN or C(S)NH$_2$; n=1 or 2; and Q is as described above.

In an embodiment of an isoxazoline as defined herein, R$^3$ is H, and R$^4$ is: —CH$_2$—C(O)—NH—CH$_2$—CF$_3$, —CH$_2$—C(O)—NH—CH$_2$—CH$_3$, —CH$_2$—CH$_2$—CF$_3$ or —CH$_2$—CF$_3$.

In a preferred embodiment of the pharmaceutical composition according to the invention, the isoxazoline is one or more selected from the group consisting of:
Fluralaner, Afoxolaner, Lotilaner, Sarolaner,
(Z)-4-[5-(3,5-Dichlorophenyl)-5-trifluoromethyl-4,5-dihydroisoxazol-3-yl]-N-[(methoxyimino)methyl]-2-methylbenzamide (CAS RN: 928789-76-8),
4-[5-(3,5-dichlorophenyl)-5-(trifluoromethyl)-4H-isoxazol-3-yl]-2-methyl-N-(thietan-3-yl)benzamide (CAS RN: 1164267-94-0), which was disclosed in WO 2009/0080250, and
5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN: 1231754-09-8), which was disclosed in WO 2010/070068.

Therefore, in a preferred embodiment of the pharmaceutical composition according to the invention, the isoxazoline is one or more selected from the group consisting of: fluralaner, afoxolaner, lotilaner, and sarolaner.

In an embodiment of the pharmaceutical composition according to the invention the isoxazoline is fluralaner. In an embodiment of the pharmaceutical composition according to the invention the isoxazoline is afoxolaner. In an embodiment of the pharmaceutical composition according to the invention the isoxazoline is lotilaner. In an embodiment of the pharmaceutical composition according to the invention the isoxazoline is sarolaner.

In an embodiment of the pharmaceutical composition according to the invention the isoxazoline is (Z)-4-[5-(3,5-Dichlorophenyl)-5-trifluoromethyl-4,5-dihydroisoxazol-3-yl]-N-[(methoxyimino)methyl]-2-methylbenzamide (CAS RN: 928789-76-8).

In an embodiment of the pharmaceutical composition according to the invention the isoxazoline is 4-[5-(3,5- dichlorophenyl)-5-(trifluoromethyl)-4H-isoxazol-3-yl]-2-methyl-N-(thietan-3-yl)benzamide (CAS RN: 1164267-94-0), which was disclosed in WO 2009/0080250.

In an embodiment of the pharmaceutical composition according to the invention the isoxazoline is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN: 1231754-09-8), which was disclosed in WO 2010/070068.

In a more preferred embodiment of the pharmaceutical composition according to the invention the isoxazoline is Fluralaner. Fluralaner has shown an extended efficacy against ectoparasites in cattle and sheep after topical administration. This showed exceptional efficacy and duration of the parasiticidal effect.

The isoxazoline for use in the invention also includes pharmaceutically acceptable salts, esters, and/or N-oxides thereof.

A pharmaceutically acceptable salt of the isoxazoline compounds of the formula (I) or (II) may be advantageous due to one or more of the salt's physical properties, such as pharmaceutical stability in differing temperatures and humidities; crystalline properties; and/or a desirable solubility in water, oil, or other solvent. Acid and base salts can typically be formed by, for example, mixing the compound with an acid or base, respectively, using various known methods in the art.

In addition, the reference to an isoxazoline compound refers equally to any of its polymorphic forms or stereoisomers.

The compounds isoxazoline compounds may exist in various isomeric forms. A reference to a compound according to this invention, an intermediate thereof and a compound corresponding to the use according to the invention always includes all possible isomeric forms of such compound.

In one embodiment the racemic form of the isoxazoline compound is present in the composition according to the invention. In another embodiment the S-enantiomer is present. In a specific embodiment the S-enantiomer of fluralaner is present.

Isoxazolines can be detected and quantified by liquid chromatography, using standard equipment and procedures.

In one embodiment the isoxazoline(s) active agents are present in the composition at a concentration of about 0.5 to about 25% (w/v). In some embodiments of the invention, the isoxazoline active agents are present in the composition as a concentration from about 1 to about 20% (w/v), about 1 to about 10% (w/v), about 2 to about 8% (w/v), or about 2, 3, 4 or 5% (w/v).

In another embodiment the isoxazoline(s) active agents are present in the composition at a concentration of about 25 and 50% w/v. In another embodiment the concentration is between 20 and 40%. (w/v).

In other embodiments, the isoxazoline active agent(s) are present in the compositions at a concentration of about 1 to about 6% (w/v), about 2 to about 5% (w/v) or about 5% (w/v).

Additional Active Ingredients

In other embodiments, the compositions may further comprise one or more additional active agents. In one embodiment, the compositions comprise at least one macrocyclic lactone active agent, including, but not limited to, avermectins or milbemycins. In some embodiments, the avermectin or milbemycin active agent is eprinomectin, abamectin, ivermectin, selamectin, milbemectin, milbemycin D, milbemycin oxime, or moxidectin.

In one embodiment the composition comprises one or more isoxazoline compounds and eprinomectin. In a specific embodiment the composition according to the invention comprises fluralaner and eprinomectin.

In one embodiment the composition comprises a combination of fluralaner with eprinomectin, or fluralaner with moxidectin. In one embodiment the composition comprises a combination of afoxolaner with eprinomectin, or afoxolaner with moxidectin. In one embodiment the composition comprises a combination of sarolaner with eprinomectin, or sarolaner with moxidectin. In one embodiment the composition comprises a combination of lotilaner with eprinomectin, or lotilaner with moxidectin.

In another embodiment, the topical compositions of the invention include a combination of an isoxazoline active agent as described in this application with an insect growth regulator (IGR) active agent. Preferably the IGR insecticide is selected from one or more of diflubenzuron, dicyclanil, lufenuron, novaluron, triflumuron, and cyromazine.

In another embodiment the topical compositions of the invention include a combination of an isoxazoline active agent as described in this application with another (one or more) ectoparasiticidal compound(s). In one embodiment such ectoparasiticidal compound is a pyrethroid. In a specific embodiment the topical composition of the invention includes a combination of fluralaner, afoxolaner, sarolaner or lotilaner with a pyrethroid, especially with deltamethin or cypermethrin, with flumethrin or permethrin, or resmethrin or lambda cyhalothrin or a combination thereof. In a specific preferred embodiment the composition include a combination of fluralaner and deltamethrin. Another preferred embodiment includes afoxolaner and deltamethrin.

In another preferred embodiment, the compositions of the invention comprise an avermectin or milbemycin and at least one endoparasiticide such as thiabendazole, oxibendazole, mebendazole, fenbendazole, flubendazole, oxfendazole, albendazole, triclabendazole, derquantel, febantel, levamisole, pyrantel, oxantel, emodepside, monepantel, atelocantel, morantel, praziquantel, epsiprantel, closantel, clorsulon, rafoxanide, and nitroxynil.

In general, the additional active agent is included in the composition in an amount of between about 0.1% and about 50% w/v. More typically, the additional active agent may be included in an amount of about 0.5% to about 25% w/v, about or about 1% to about 10% w/v.

In other embodiments of the invention, the additional active agent (e.g. as described above) may be included in the composition to deliver a dose of about 5 µg/kg bodyweight to about 50 mg per kg bodyweight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, any one of the additional active agent(s) is included in a dose between about 0.5 mg/kg to about 50 mg/kg.

It will be understood that the ability of an active agent to be distributed either topically or transdermally after pour-on administration is dependent both on the physicochemical characteristics of the compound and also on the non-active excipients of the composition.

Examples of non-active excipients that influence the transdermal distribution are dermal penetration enhancers or "permeation enhancers". These are typically used in compositions designed to deliver active compounds transdermally.

A dermal penetration enhancer (or permeation enhancer) is a pharmaceutically acceptable carrier that promotes the absorption or penetration of the compound through the skin into the blood stream, other bodily fluids (lymph), and/or body tissue (fat tissue).

The composition according to the invention comprises menthol as dermal penetration enhancer.

Menthol is available as one of two enantiomers or as racemate. The naturally occurring material is the levorotatory form (−)-menthol (or l-menthol). Synthetic menthol is racemic, consisting of equal amounts (−)-menthol and (+)-menthol (or d-menthol). Preferably Levomenthol EP (European Pharmacopoeia) or l-Menthol (USP) is used in the composition of the invention. Alternatively, another terpenoids such as eucalyptol, camphor, d-limonene, nerolidol, 1-8 Cineole and mixtures thereof is additionally present in the composition. Alternatively, a combination of menthol and eucalyptol is used.

In particular embodiments of the invention, the menthol is present in amounts from about 2 to about 20% w/v of composition, particularly from about 5 to about 15% w/v or particularly from about 6 to about 12% w/v or about 10% w/v.

In one embodiment the transdermal liquid preparation of the invention includes two or more dermal penetration enhancers.

Permeation enhancers constitute various classes of compounds including certain solvents such as dimethylsulfoxide (DMSO), isopropyl myristate, dipropylene glycol pelargonate, silicone oil, aliphatic esters, triglycerides, and fatty alcohols pyrrolidones, ethanol, propylene glycol, ethyl acetate, dimethylacetamide, and others that are capable of disrupting the barrier function of the stratum corneum.

Non-limiting examples of a suitable dermal penetration enhancer include, but are not limited to, terpenoids such as menthol, eucalyptol, camphor, d-limonene, nerolidol, 1-8 Cineole and mixtures thereof, saturated or unsaturated fatty acid esters or diesters of propylene glycol or esters, diesters or triesters of glycerol, saturated or unsaturated fatty acids, saturated or unsaturated fatty alcohols, xylene, isopropyl myristate, or mixtures thereof.

Particularly, the dermal penetration enhancer is a combination of menthol with xylene and/or D-limonene and/or isopropyl myristate. In one embodiment the dermal penetration enhancer is menthol or eucalyptol or a combination thereof. In another embodiment the dermal penetration enhancer is menthol.

Other substances have also been shown to increase the flux of certain active agents through the skin. These include lipophilic compounds such as laurocapram (Azone); fatty acids or alcohols such as oleic acid, oleyl alcohol, linoleic acid and the like; certain fatty acid esters such as isopropyl myristate, methyl noanoate, methyl caprate and others. Mixtures of certain permeation enhancers with propylene glycol are also known to improve the delivery of certain active ingredients.

Other permeation enhancers are dimethyl isosorbide and glycol ethers such as, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether.

In particular embodiments of the invention, the dermal penetration enhancer is present in amounts from about 2 to about 90% w/v of the transdermal liquid preparation, particularly from about 5 to about 80% w/v or particularly from about 10 to about 70% w/v. In one embodiment menthol is present at 10% w/v. In another embodiment menthol is present at about 10% w/v wand eucalyptol at 10% w/v.

The optional second dermal penetration enhancer is particularly present in an amount from about 2 to about 70% w/v of the transdermal liquid preparation, particularly from about 5 to about 50% w/v, or more particularly from about 10 to about 40% w/v.

The pharmaceutically acceptable carrier comprises a solvent system comprising suitable carriers or diluents commonly used in the composition art including solvents or mixtures of solvents.

Certain solvents suitable for topical compositions may be characterized as having good spreading properties while other solvents for topical compositions may be characterized by an ability to enhance permeation of active agents through the skin barrier into the systemic circulation In certain embodiments of the invention, the compositions will comprise mixtures of solvents that will enhance the spreading ability and/or the permeation enhancing ability of the composition.

In particular compositions of the invention, the solvent is present in an amount from about 10 to about 90% by weight of the transdermal liquid preparation, particularly, from about 20 to about 80%, from about 25 to about 70%, about 70% w/v, 60% w/v.

In one embodiment the solvent system comprises at least one pyrrolidone solvent and at least one volatile solvent, especially a volatile alcohol solvent In another embodiment the solvent system comprises instead or in addition to the volatile solvent one or more of glycerol esters, propylene glycol esters, or another non-volatile solvent.

In another embodiment the solvent system comprises one or more of glycerol esters, propylene glycol esters.

In embodiments of the invention, the pyrrolidone solvent is present in amounts from about 5 to about 50% w/v of the composition, particularly from about 5 to about 40% w/v or particularly about 5, about 10 or about 35% w/v.

Particularly, the pyrrolidone solvent comprises 2-pyrrolidone, N-methyl pyrrolidone (NMP), or mixtures thereof. In one embodiment the pyrrolidone solvent is 2-pyrrolidone. In another embodiment the pyrrolidone solvent is NMP.

In particular embodiments of the invention, the 2-pyrrolidone or NMP is present in amounts from about 5 to about 50% w/v of the composition, particularly from about 5 to about 40% w/v or particularly about 5, about 10 or about 35% w/v.

In embodiments of the invention, the volatile solvent, especially an alcohol solvent is present in amounts from about 5 to about 60% w/v of the composition, particularly from about 5 to about 50% w/v or particularly from about 20 to about 45% w/v or particularly about 33-35%, about 54-55 or about 10% w/v.

Particularly, the volatile solvent, especially an alcohol solvent comprises a volatile alcohol, such as e.g. ethyl alcohol, methanol, or isopropyl alcohol (isopropanol) or mixtures thereof. In one embodiment the alcohol solvent is isopropyl alcohol.

A volatile substance is in general easily evaporated at normal temperatures and easily become vapors or gases. The European Union defines a volatile organic compound as "any organic compound having an initial boiling point less than or equal to 250° C. (482° F.) measured at a standard atmospheric pressure of 101.3 kPa.

In particular embodiments of the invention, isopropyl alcohol is present in amounts from about 5 to about 60% w/v of the composition, particularly from about 5 to about 50% w/v or particularly from about 20% to about 45% w/v or particularly about 33-35%, about 54-55% or about 10% w/v.

In another embodiment the solvent system comprises at least one pyrrolidone solvent and at least one volatile solvent, especially an alcohol solvent and an additional solvent.

In another embodiment the solvent system comprises least one pyrrolidone solvent and at least one of glycerol esters, propylene glycol esters, or another non-volatile solvent.

Non-limiting examples of suitable solvents include, but are not limited to, solvents e.g. water, a pyrrolidone solvent, such as 2-pyrrolidone, N-methyl-2-pyrrolidone, and/or mixtures thereof, and glycol ethers such as ethylene glycol monoethyl ether, diethylene glycol monoethyl ether, or dipropylene glycol monoethyl ether, ethyl lactate, glycol ether such as diethylene glycol monoethyl ether (DE-GMEE), glycerin, dimethylisosorbide, triacetin, propylene glycol, glycol ethers such as polyethylene glycols (PEG) having an average molecular weight between about 200 and 1000, dimethylisosorbide, PEG esters of carboxylic acids and dicarboxylic acids and PEG esters of fatty acids, glycerol esters including triacetin, caprylic/capric triglycerides (Miglyol 812®) and the like; glycerol ethers including glycerol formal; propylene glycol dicaprylate/dicaprate (Miglyol 840®), lauryl lactate, diisopropyl adipate (DIPA, also known as CERAPHYL 230), diisobutyl adipate, dimethyl isosorbide (DMI), acetyltributyl citrate, oleic acid; carboxylic acid esters including esters of diacids, ketones including acetone, methylisobutyl ketone (MIK), methyl ethyl ketone, acetonitrile, C1-C12 alcohols including benzyl alcohol, methanol, ethyl alcohol, isopropanol isopropanol, (1,2-propanediol, isopropyl alcohol), and butanol; aromatic ethers such as anisole; amides including dimethylacetamide, monomethylacetamide and dimethylformamide; dimethyl sulfoxide (DMSO), ethylene glycol, propylene glycol, a glycol carbonate including, but not limited to, propylene carbonate and, butylene carbonate; C1-C12 alkyl esters of carboxylic acids including butyl or octyl acetate and benzyl acetate; C1-C12 alkyl esters of dicarboxylic acids; aryl esters including benzyl benzoate, ethyl benzoate and the like; and diethyl phthalate, diester of a dicarboxylic acid is diethyl sebacate or diisopropyl adipate, ethylene glycol (EG), propylene glycol (PG), liquid polyoxyethylene glycols (PEGs) of various grades including PEG 400, EG or PG monocaprylate, EG or PG caprylate, EG or PG monolaurate, EG or PG dicaprylate/dicaprate, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, or a combination thereof; an ether including, but not limited to, dimethyl isosorbide; an ester or di-ester including, but not limited to, triacetin, lauryl lactate, glycerol formal, diethyl sebacate, diisopropyl sebacate, diisopropyl adipate, dibutyl adipate, PG monocaprylate, PG caprylate, PG monolaurate, PG dicaprylate/dicaprate, isopropyl palmitate, or mixtures thereof.

In one embodiment the composition does not include any volatile solvent. In one embodiment the composition comprises fluralaner, a penetration enhancer (menthol), a solvent (pyrrolidone), and glyceryl monocaprylate, preferably at 20-80% v/v, without a volatile solvent.

It has been found that the topical compositions of the present invention comprising an isoxazoline active agent in a carrier comprising a lipophilic solvent or lipophilic solvent system result in very good efficacy against ectoparasites for an extended duration of time. Although not wishing to be bound by theory, it is believed that the non-active excipients in the topical compositions of the invention promote the containment of the isoxazoline active agent within the skin for longer periods of time while allowing the active agent to constantly diffuse into the circulatory system at a rate that provides the required concentration of the active in the blood stream to be efficacious against ectoparasites for a longer period of time.

This is contrary to the approaches used with typical topical compositions that are designed to enhance the transdermal passage of compounds quickly to obtain the desired biological effect, e.g. a fast inflammatory effect in case of NSAID's with no desire for an extended duration, especially in case of livestock animals because of the risk of residues.

As vehicle or diluent plant oils could be used such as, soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons including limonene or alternatively, for example, medium-chain (such as $C_8$ to $C_{12}$) triglycerides, such as Miglyol 812 or alternatively Miglyol 840 or mixtures thereof.

In one embodiment the pour-on or spot-on isoxazoline composition comprises glyceryl monocaprylate.

In another embodiment, the pharmaceutically acceptable carrier comprises $C_4$-$C_{22}$ fatty acids or esters thereof, including esters with $C_6$-$C_{20}$ long chain alcohols, $C_1$-$C_{12}$ alcohols, $C_1$-$C_4$ alcohols or $C_3$-$C_8$ alcohols; $C_{10}$-$C_{18}$ saturated fatty acids or esters thereof, including esters with $C_6$-$C_{20}$ long chain alcohols, $C_1$-$C_{12}$ alcohols, $C_1$-$C_4$ alcohols or $C_3$-$C_8$ alcohols; $C_1$-$C_{18}$ unsaturated fatty acids or esters thereof, including esters with $C_6$-$C_{20}$ long chain alcohols, $C_1$-$C_{12}$ alcohols, $C_1$-$C_4$ alcohols or $C_3$-$C_8$ alcohols; monoesters or diesters of $C_6$-$C_{16}$ aliphatic carboxylic acids and carboxylic diacids, including esters with $C_6$-$C_{20}$ long chain alcohols, $C_1$-$C_{12}$ alcohols, $C_1$-$C_4$ alcohols or $C_3$-$C_8$ alcohols, or mixtures thereof. In other embodiments, the carrier may include $C_1$-$C_{10}$, $C_1$-$C_8$ or $C_1$-$C_6$ alcohols or esters thereof.

In another embodiment, the compositions of the invention comprise polar solvents. In another embodiment the composition comprises aromatic alcohols or esters thereof. In one preferred embodiment, the topical compositions of the invention may include isopropyl alcohol or benzyl alcohol as a solvent. In one embodiment the topical compositions of the invention include isopropyl alcohol. Alternatively, no volatile solvent is included in the composition, but a glycerol ester.

In preferred embodiments the pour-on or spot-on isoxazoline composition comprises vehicles selected from the group consisting of diethyl sebecate, dibutyl sebacate, saturated or unsaturated fatty acid mono- and di-esters of propylene glycol or mono-, di- and tri-esters of glycerol with alkyl chain lengths from C8-C14, saturated fatty acids with alkyl chain lengths from C8-C14, unsaturated fatty acids with alkyl chain lengths from C14-C22, saturated fatty alcohols with alkyl chain lengths from C8-C14, and unsaturated fatty alcohols with alkyl chain lengths from C14-C22.

In another preferred embodiments the pour-on or spot-on isoxazoline composition comprises vehicles selected from the group consisting of, saturated or unsaturated fatty acid mono- and di-esters of propylene glycol or mono-, di- and tri-esters of glycerol with alkyl chain lengths from C8-C14, saturated fatty acids with alkyl chain lengths from C8-C14, unsaturated fatty acids with alkyl chain lengths from C14-C22, saturated fatty alcohols with alkyl chain lengths from C8-C14, and unsaturated fatty alcohols with alkyl chain lengths from C14-C22.

In one preferred embodiment, the pour-on or spot-on isoxazoline composition comprises the preferred vehicles propylene glycol dicapryocaprate, glyceryl monocaprylate, and mixtures thereof.

In a preferred embodiment, the topical compositions of the invention comprising isoxazoline active agent(s) are dissolved in a pharmaceutically acceptable carrier comprising one or more solvents. In some embodiments of the invention solvents include, but are not limited to, dimethyl isosorbide glycofurol, glycerol formal (methylidinoglycerol or glycerin formal), triacetin, liquid polyethylene glycols including PEG 200, or 400, diisopropyl adipate isopropyl palmitate, silicone fluid; propylene glycol (or other aliphatic dihydric alcohols), benzyl alcohol, propylene glycol esters including propylene glycol dicaprylate/dicaprate, propylene carbonate, propylene glycol monocaprylate, propylene glycol dicaprylate, propylene glycol monolaurate and propylene glycol dilaurate; alkyl esters of dicarboxylic acids including diethyl sebacate, diisopropyl sebacate; and esters or diesters of fatty acid, or combinations thereof.

In an embodiment of the invention, the compositions of the invention may include surfactants. The surfactants may be anionic, cationic, non-ionic or amphoteric surfactants.

Anionic surfactants include, but are not limited to, alkaline stearates; calcium stearate; triethanolamine stearate; sodium abietate; alkyl sulfates; sodium dodecylbenzenesulphonate, sodium dioctylsulphosuccinate; fatty acids, and the like.

Examples of cationic surfactant include, but are not limited to, water-soluble quaternary ammonium salts of formula; cetyltrimethylammonium bromide and octadecylamine hydrochloride.

Non-ionic surfactants that may be used in the compositions include, but are not limited to, polyoxyethylenated (PEGylated) esters including, but not limited to, sorbitan esters and fatty acid esters; polyethylene glycol stearate, polyoxyethylenated derivatives of castor oil, polyglycerol esters, polyoxyethylenated fatty alcohols, polyoxyethylenated fatty acids, and copolymers of ethylene oxide and propylene oxide including, but not limited to, block copolymers of ethylene oxide and propylene oxide such as poloxamers and the like (e.g. Lutrol® F grades and L grades from BASF including Lutrol® F68, F87, F108 and F127).

Further example of surfactants include, but are not limited to, CAPRYOLT™ 90 (propylene glycol monocaprylate), CAPRYOLT™ PGMC (propylene glycol monocaprylate) which are oily liquids having an HLB (hydrophilic-lipophilic balance) of 6 and 5, respectively. Topically they can be used as a co-surfactant in microemulsions and as a solubilizer/penetration enhancer. As used herein, HLB values have the following general meanings: compounds with a HLB value of <10 tend to be lipid soluble (water insoluble) and solvents with a HLB>10 tend to be water soluble. Surfactants having HLB between 4 and 8 are typically useful as anti-foaming agents. Surfactants having HLB from 7 to 11 may be useful as W/O (water in oil) emulsifiers. HLB of 12 to 16 typically indicates a surfactant may be useful in oil in water emulsions, and HLB of 11 to 14 is indicative of a wetting agent. HLB of 12 to 15 is typical of detergents, and HLB of 16 to 20 indicates a solubilizer or hydrotrope. There is significant an overlap of ranges/uses, and a skilled person well understands that the HLB value alone cannot be used to predict whether a particular surfactant will serve a specific purpose (e.g. anti-foaming agent, emulsifier, wetting agent, solubilizer, hydrotrope). Therefore, in general, determination of a suitable system of solvent, active agent, surfactant (s) and other excipients necessarily involves non-routine experimentation and inventive effort.

The compositions may also include surfactants such as oleoyl macrogolglycerides (polyoxylglycerides, for example, LABRAFIL® M1944CS and LABRAFIL® M2125CS both having an HLB of 4). These compounds may also be used, for example, as oily phase for emulsions, microemulsions, and as penetration enhancers.

In another embodiment, the polyoxylglycerides may include polyethyleneglycol caprylic/caprylic glycerides such as LABRASOL® (HLB of 14. Topically it is used as a surfactant in microemulsions, and can also act as a solubility/penetration enhancer in topical compositions.

In another embodiment the surfactant is LAUROGLYCOL™ 90 (propylene glycol monolaurate) having an HLB of 5. It is a co-surfactant for microemulsions in topical compositions and can also act as a solubilizer/penetration enhancer in topical compositions. In some embodiments, the surfactant is PLUROL® OLEIQUE CC497 (polyglyceryl oleate), having an HLB of 6.

In some embodiments of the invention, compositions are provided wherein the carrier comprises solvents that exhibit both good spreading and permeation characteristics. In other embodiments, the invention provides compositions wherein the carrier comprises solvents that exhibit good spreading characteristics. In still another embodiment of the invention, compositions are provided wherein the carrier vehicle comprises solvents that enhance the permeation of the active agent through the skin into the systemic circulation.

In some instances, solvents may include both good spreading and good permeation characteristics. Propylene glycol dicaprylate/dicaprate e.g. Miglyol 840 has both good spreading and permeation characteristics.

In particular embodiments of the invention, the Propylene glycol dicaprylate/dicaprate is present in amounts from about 2 to about 90% w/v of the composition, particularly from about 5 to about 80% w/v or particularly from about 10 to about 70% w/v.

Excipients that may also promote the containment of the active agent in the skin for longer periods of time and may be included in the compositions of the invention include, but are not limited to, mixed esters of sucrose and carboxylic acids including sucrose acetate isobutyrate (SAIB) and the like; low temperature melting waxes, hydrogenated vegetable oils, caprylic/capric glycerides; glycerol esters, including for example, triacetin, glycerol monooleate, glycerol monolinoleate, glycerol stearate, glyceryl distearate and the like; triglycerides, including for example, caprylic, capric/myristic/stearic triglyceride; thermoreversible polymers, such as Pluronic and poloxamers, including for example, Lutrol F 127 by itself or in mixture with other poloxamers; or a combination thereof.

The addition of one or more of additional other solvents may be desirable to alter the viscosity of the composition in order to provide a product with appropriate characteristics for pour-on application.

The viscosity of pour on compositions can be measured by methods known in the art.

Suitable viscosity modifying agents include, without limitation, water, ethanol, isopropanol, propylene glycol, dimethylisosorbide, triacetin, or glycerol, added in an appropriate quantity known to one skilled in the art.

Suitable exemplary polymers ("polymeric agents") for gelling and/or adhering that may be used in the compositions of the invention include, but are not limited to, colloidal silicone dioxide, ethyl cellulose, methyl cellulose, methacrylic esters copolymers, carboxylated vinyl acetate, and polyvinylpropylene (PVP)/Vinyl acetate copolymers, Poloxamer 124, Poloxamer 188, Polybutene, Povidone K17 and Povidone K90. The inventive compositions may contain other inert ingredients such as colorants, antioxidants, preservatives, pH stabilizers, chelating agents, and viscosity modifying agents.

Preservatives, such as the parabens (methylparaben and/or propylparaben), are suitably used in the composition in amounts ranging from about 0.01 to about 2.0% w/v, with about 0.05 to about 1.0% w/v being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like.

Exemplary chelating agents include without limitation edetate disodium and EDTA.

Antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy anisole), BHT (butylated hydroxy toluene), BHA and citric acid, monothioglycerol, tert-butyl hydroquinone (TBHQ), and the like, may be added to the present composition.

The antioxidants are generally added to the composition in amounts of from about 0.01 to about 2.0% w/v, based upon total weight of the composition, with about 0.05 to about 1.0% w/v being especially preferred.

In order to prevent degradation of any of the active ingredients in the compositions of the present invention, the addition of at least one stabilizer has been found to be advantageous.

In an embodiment, an additional constituent for the composition according to the invention is a pharmaceutically acceptable coloring agent, such as a dye or pigment or a combination of different dyes or pigments. This will allow visual monitoring of the treated animals by detecting the coloring agent's color on the back of the animal.

Colorants for use in the present invention are those commonly known in the art. Such a coloring agent should of course be allowed for administration to food producing livestock animals. Suitable coloring agents are those allowed under the US Federal Food, Drug, and Cosmetic Act (FD&C) such as FD&C Blue no 1, FD&C Yellow no 5 or natural food dyes such as Chlorophyllin (green), or a mixture of any of the foregoing. Preferred ranges include from about 0.01% to about 2% (w/v), more preferably from about 0.01% to about 0.5% (w/v).

Optionally, the composition may also contain an anti-foaming agent, such as for example, simethicone emulsion 30% USP, sodium oleate, sodium caprylate or mixtures thereof. The antifoaming agent is present in sufficient concentration to prevent foam formation when the composition of the instant invention is diluted with water. In the instant invention the simethicone emulsion may be present at concentration of from about 0.2% w/v to about 1% w/v. In some embodiments, the simethicone emulsion is present at a concentration of about 0.5% w/v.

Optionally, a fragrance may be added to any of the compositions of the invention.

Further aspects regarding composition of drugs and various excipients are found in, for example, Gennaro, A. R., et al., eds., Remington: The Science and Practice of Pharmacy (Lippincott Williams & Wilkins, 20th Ed., 2000).

In one embodiment the liquid veterinary pour-on composition, comprises:
a) from about 0.5% to about 15% w/v of the isoxazoline compound;
b) from about 5% to about 15% w/v of menthol;
c) from about 10% to about 50% w/v of isopropyl alcohol;
d) from about 10% to about 40% w/v of a pyrrolidone solvent; and
e) from about 2% to about 50% w/v of a propylene glycol dicaprylate/dicaprate.

In another embodiment the liquid veterinary pour-on composition, comprises:
a) from about 0.5% to about 15% w/v of the isoxazoline compound;
b) from about 5% to about 15% w/v of menthol;
c) from about 10% to about 40% w/v of a pyrrolidone solvent; and
d) from about 2% to about 70% w/v of a propylene glycol dicaprylate/dicaprate.

In another embodiment the liquid veterinary pour-on composition, comprises:
a) from about 0.5% to about 15% w/v of the isoxazoline compound;
b) from about 5% to about 15% w/v of menthol;
c) from about 10% to about 50% w/v of a glycerol ester especially glyceryl monocaprylate;
d) from about 10% to about 40% w/v of a pyrrolidone solvent; and
e) from about 2% to about 50% w/v of a propylene glycol dicaprylate/dicaprate.

In a preferred embodiment the liquid veterinary pour-on composition comprises about 2 to about 5% w/v of the isoxazoline compound, and the carrier comprises about 10% w/v of menthol, between about 35 and about 55% w/v of isopropyl alcohol, between about 5 and about 35% w/v of 2-pyrrolidone and/or about 10% w/v of propylene glycol dicaprylate/dicaprate.

In an alternative embodiment the composition comprises about 2 to about 5% w/v of the isoxazoline compound, and the carrier comprises about 10% w/v of menthol, between about 5 and about 35% w/v of 2-pyrrolidone and/or about 10% w/v of propylene glycol dicaprylate/dicaprate.

In another preferred embodiment the liquid veterinary pour-on composition comprises about 3 to 5% w/v r about 2, about 3, or about 5% w/v of the isoxazoline compound and the carrier comprises about 35 or about 55% w/v of isopropyl alcohol and about 5 or about 35% w/v of 2-pyrrolidone or NMP.

In another preferred embodiment the liquid veterinary pour-on composition comprises about 3 to 5% w/v or about 2, about 3, or about 5% w/v of the isoxazoline compound and the carrier comprises about
or about 55% w/v of glyceryl monocaprylate and about 5 or about 35% w/v of 2-pyrrolidone or NMP.

Of special note are compositions comprising 5% w/v fluralaner, optionally 0.5% eprinomection, a pyrrolidone solvent (preferably 2 pyrolidone), L menthol, Miglyol 840 and glycerol monocaprylate.

Of special note are compositions comprising 5% w/v fluralaner, optionally 0.5% eprinomection, a pyrrolidone solvent (preferably 2 pyrolidone), L menthol, Miglyol 840 and isopropylalcohol.

In a method of preparing the composition of the present invention, the excipients and the isoxazoline compound is mixed until all solids are dissolved. An additional solvent to bring the composition to final volume may be added if needed. Additives, such as those listed above, may also be included in the vessel and mixed into the composition. The order of addition of the above excipients, solvents and additives is not critical.

In other embodiments, the compositions of the invention may be in the form of oil-in-water or water-in-oil emulsions. In some embodiments the oily phase may be a vegetable oil, for example, olive oil or arachis oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan mono oleate, and condensation products of the said partial esters with ethylene oxide, for example, polyoxy ethylene sorbitan mono oleate, and the like. In some embodiments, the emulsions may also contain preservatives.

In another embodiment the composition of the invention is in the form of a microemulsion. Microemulsions are well suited as the liquid carrier vehicle. Microemulsions are typically quaternary systems comprising an aqueous phase, an oily phase, a surfactant and a co-surfactant. They are usually translucent and isotropic liquids. Microemulsions are composed of stable dispersions of microdroplets of the aqueous phase in the oily phase or conversely of microdroplets of the oily phase in the aqueous phase. The size of these microdroplets is typically less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides. In another embodiment of the oily phase, the triglycerides are medium-chain triglycerides, for example $C_5$-$C_{10}$ caprylic/capric triglyceride. In another embodiment, the oily phase will represent a % v/v range selected from the group consisting of about 1 to about 20%; about 2 to about 15%; about 7 to about 10%>; and about 8 to about 9% v/v of the microemulsion.

The aqueous phase typically includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 10% v/v or about 1 to about 4% v/v in the microemulsion.

Surfactants for the microemulsion typically include diethylene glycol monoethyl ether, dipropyelene glycol monomethyl ether, polyglycolyzed $C_8$-$C_{10}$ glycerides or polyglyceryl-6 dioleate, or a combination of these surfactants. In addition to these surfactants, the co-surfactants include short-chain alcohols, such as ethanol and propanol. Additionally, poloxamers and Pluronic F127 can be used as surfactants.

Some compounds are common to the three components discussed above, i.e., aqueous phase, surfactant and co-surfactant. However, it is well within the skill level of the practitioner to use different compounds for each component of the same composition.

The pharmaceutically acceptable carrier can optionally contain a crystallization inhibitor such as the crystallization inhibitors described below, or mixtures thereof, to inhibit the formation of crystals or precipitate of the active components (e.g. the isoxazoline compounds).

The veterinarily and/or pharmaceutically acceptable carrier will generally comprise a diluent or vehicle in which the active agents are soluble. It will be apparent to those of skill in the art that the carrier or diluent of the topical compositions must be able to deliver the active agents to the targeted location without the active agents precipitating from solution or forming crystals. In some embodiments, the carrier or diluent of the compositions will be suitable to avoid precipitation or crystallization of the active agents. In other embodiments, the compositions may include a crystallization inhibitor component in addition to the carrier or diluent.

Crystallization inhibitors which are useful for the invention include but are not limited to: (a) polyvinylpyrrolidone, polyvinyl alcohols, copolymers of vinyl acetate and of vinylpyrrolidone, 2-pyrrolidone including N-methylpyrrolidone, dimethylsulfoxide, polyethylene glycols, co-polymers of polyoxyethylene and polyoxypropylene, benzyl alcohol, mannitol, glycerol, sorbitol or polyoxyethylenated esters of sorbitan; lecithin or sodium carboxymethylcellulose; or acrylic derivatives, such as polymers derived from acrylic monomers including polyacrylates or polymethacrylates; and, a solvent as described herein that inhibits the crystallization of the active agent, and similar compounds;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulphosuccinate; or fatty acids (e.g. coconut oil);

(c) cationic surfactants, such as water-soluble quaternary ammonium salts of formula N R'R"R'"R""Y<">, in which the R radicals are identical or different optionally hydroxylated hydrocarbon radicals and Y is an anion of a strong acid, such as halide, sulfate and sulfonate anions; cetyltrimethylammonium bromide is one of the cationic surfactants which can be used;

(d) amine salts of formula N HR'R'R'" Y<">, in which the R radicals are identical or different optionally hydroxylated hydrocarbon radicals and Y<"> is the anion of a mineral or organic acid; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil including hydrogenated castor oil and its derivatives, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. Other crystallization inhibitor pairs include a polyethylene glycol and a non-ionic surfactant. Additional crystallization pairs including other mixtures are also contemplated. These agents can be selected from the compounds mentioned above as crystallization inhibitor.

In some embodiments, the crystallization inhibitor can be present in a proportion of about 1 to about 30% (w/v). Typically, the crystallization inhibitor may be present in a proportion of about 1% to about 20% (w/v), about 1% to about 10% (w/v), or about 5% to about 15% (w/v). Acceptable inhibitors are those whose addition to the composition inhibits the formation of crystals of the active agents when the composition is applied. In some embodiments, compositions may include compounds that function as crystallization inhibitors other than those listed herein. In these embodiments, the suitability of a crystallization inhibitor may be determined by testing if it will sufficiently inhibit the formation of crystals so that a sample containing 10% (w/v) of the isoxazoline active agent in a solvent as described above with 10% (w/v) of the crystallization inhibitor will result in less than 20, preferably less than 10 crystals when placed on a glass slide at 20° C. for 24 hours.

Pour-on compositions also (or alternatively) may comprise one or more spreading agents. These substances act as carriers that assist in distributing an active ingredient over the animal recipient's coat or skin. They may include, for example, isopropyl myristate, dipropylene glycol pelargonate, silicone oils, fatty acid esters, triglycerides, and/or fatty alcohols.

Various spreading oil/solvent combinations also may be suitable, such as, for example, oily solutions, alcoholic and isopropanolic solutions (e.g., solutions of 2-octyl dodecanol or oleyl alcohol), solutions of esters of monocarboxylic acids (e.g., isopropyl myristate, isopropyl palmitate, lauric acid oxalic ester, oleic acid oleyl ester, oleic acid decyl ester, hexyl laurate, oleyl oleate, decyl oleate, and caproic acid esters of saturated fatty alcohols having a carbon chain of 12 to 18 carbons), solutions of esters of dicarboxylic acids (e.g., dibutyl phthalate, diisopropyl isophthalate, adipic acid diisopropyl ester, and di-n-butyl adipate), or solutions of esters of aliphatic acids (e.g., glycols). When the composition comprises a spreading agent, it also may be advantageous to include a dispersant, such as, for example, pyrrolidin-2-one, N-alkylpyrrolidin-2-one, acetone, polyethylene glycol, or an ether or ester thereof, propylene glycol, or synthetic triglycerides.

In some embodiments of the invention, an emollient and/or spreading and/or film-forming agent may be added to the topical compositions of the invention. Emollients, spreading agents and film forming agents are well known in the art. In various embodiments, the emollients, spreading agents and film forming agents that may be used in the topical compositions include the components listed in (a) to (g) above, including polymer derivatives such as polyvinylpyrrolidone, polyvinyl alcohols and copolymers of vinyl acetate and vinylpyrrolidone; anionic surfactants; cationic surfactants; non-ionic surfactants; amphoteric surfactants; amine salts, and combinations thereof. In one embodiment, the emollient is used in a proportion of from about 0.1 to about 10%, or about 0.25 to about 5% (w/v).

Topical administration of the inventive composition results in effective blood plasma concentrations, Topical application of the inventive compositions enables effective delivery of the active agent transdermally through the skin into the systemic circulation and on the surface of the animal at a concentration sufficient to provide excellent and long duration efficacy against ectoparasites. The compositions of the invention achieve distribution of the active agent both topically over the hair coat of the animal and also transdermally into the blood stream. In this embodiment, the topical compositions provide a high level of efficacy at unexpectedly low plasma concentrations of the isoxazoline active agent.

In some embodiments of the invention, the compositions are formulated to control the rate of permeation of the isoxazoline compound in order to maintain efficacious levels of the active in the plasma for a prolonged period of time and significantly extend the duration of efficacy.

The liquid preparation according to the invention has a desirable absolute systemic bioavailability to facilitate this excellent and long duration efficacy against ectoparasites. Bioavailability is a measurement of the extent of a therapeutically active drug that reaches the systemic circulation. It is expressed as the letter F. Absolute bioavailability measures the availability of the active drug in systemic circulation after non-intravenous (i.e., after oral, transdermal, subcutaneous administration).

The absolute bioavailability is the dose-corrected area under curve (AUC) non-intravenous divided by AUC intravenous. For example, the formula for calculating F for a drug administered by the subcutaneous route (sc) is given below.

$$F = \frac{[AUC]_{po} * dose_{IV}}{[AUC]_{IV} * dose_{po}}$$

In one embodiment the isoxazoline compound in the composition according to the invention has an absolute systemic bioavailability of 5 to 10% after pour-on or spot-on administration. In one embodiment the absolute systemic bioavailability is between 2 and 10%. In another embodiment the absolute systemic bioavailability is between 30 and 40%. In another embodiment the absolute systemic bioavailability is between 20 and 30%. In another embodiment the absolute systemic bioavailability is higher than 30%.

Methods of Treatment

In another aspect of the invention, a method for preventing or treating a parasite infestation/infection in an animal is provided, comprising administering to the animal a topical composition comprising an effective amount of at least one isoxazoline active agent together with a pharmaceutically acceptable carrier that is suitable for pour-on and/or spot-on application to the skin of the animal. The compositions or compositions of the invention have long-lasting efficacy against ectoparasites (e.g. fleas and ticks) and in certain embodiments may also active against endoparasites that harm animals.

In one embodiment of the invention, methods for the treatment or prevention of a parasitic infestation or infection in a domestic animal are provided, which comprise administering a topical composition comprising an effective amount of at least one isoxazoline active agent to the animal as a pour-on or spot-on. Ectoparasites against which the methods and compositions of the invention are effective include, but are not limited to, fleas, ticks, mites, mosquitoes, flies and lice. In certain embodiments, wherein the compositions include one or more additional active agents that are active against internal parasites, the compositions and methods of the invention may also effective against endoparasites including, but not limited to, cestodes, nematodes, hookworms and roundworms of the digestive tract of animals and humans.

The ectoparasites treated include but are not limited to fleas, ticks, mites, mosquitoes, flies, lice, blowfly and combinations thereof.

In another embodiment for the treatment against ectoparasites, the ectoparasite is a tick from the genera *Boophilus/Rhipicephalus, Dermacentor, Ixodes, Boophilus, Amblyomma, Haemaphysalis, Hyalomma* especially *Boophilus (Rhipicephalus)*, especially those of the species *microplus* (cattle tick), *R. decoloratus* and *R. annulatus*.

*Rhipicephalus microplus, R. decoloratus* and *R. annulatus* are single host ticks, this means all three stages of the lifecycle are spent on the same animal.

Multi-host ticks means the tick drops to the ground after each stage and the re-attaches to another host and the species of host between the different stages may differ are e.g. *Amblyoma cajennense, Ixodes holocyclus*, i.e. paralysis tick: *H. longicornis, Rhipicephalus appendiculatus* and *Amblyoma haebraum, Dermacentor albipictus, Amblyoma maculatum, Amblyoma andersoni, Ixodes ricinus, Dermacentor marginatus*.

Additional examples of ectoparasites include but are not limited to flies causing myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa).

Biting flies namely those whose adult constitutes the parasite, such as *Haematobia irritans* (horn fly), *Haematobia irritans exiqua* (buffalo fly) and *Stomoxys calcitrans* (stable fly).

Sucking lice consume a blood meal from their host and are more important in transmitting pathogens. Chewing or biting lice ingest fur and skin and sometimes blood from their host, important lice parasites are the cattle biting louse (*Bovicola bovis*), the longnosed cattle louse (*Linognathus vituli*), the little blue cattle louse (*Solenopotes capillatus*), the shortnosed cattle louse (*Haematopinus eurysternus*), and the cattle tail louse (*Haematopinus quadripertusus*) and the sheep biting louse of sheep and goats (*Bovicola ovis*).

Important mite parasites are e.g. *Chorioptes bovis, Sarcoptes scabiei* and *Psoroptes ovis*

The above list is not exhaustive and other ectoparasites are well known in the art to be harmful to animals, especially livestock animals, especially ruminants, more especially cattle or sheep. These include, for example migrating dipterous larvae.

It has been surprisingly found that the pour-on composition of the invention is effective to control one or more of these parasites.

In some embodiments of the invention, especially in case the isoxazoline compound is combined with another active ingredient, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris*, and *Trichostrongylus*, among others.

In another preferred embodiment, the methods and compositions of the invention are used for the treatment or prevention of parasitic infections and infestations in cattle or sheep. When treating livestock animals such as cattle or sheep, the methods and compositions are particularly effective against *Rhipicephalus (Boophilus) microplus, Haematobia irritans* (horn fly), *Stomoxys calcitrans* (stable fly), and (sheep) myiases caused by blowflies such as *Lucilia sericata*, (European green blowfly), *Lucilia cuprina* (Green blowfly or Australian sheep blowfly, known as blowfly strike in Australia, New Zealand and South Africa) *Chrysomya rufifacies* (Hairy maggot fly), *Chrysomya varipes* (Small green blowfly), *Calliphora stygia* (Common brown blowfly), *Calliphora augur* (Lesser brown blowfly (eastern), *Calliphora novicia* (Lesser brown blowfly (western).

Important lice species in ruminant animals, such as cattle and sheep, that can be controlled by the inventive compositions are *Bovicola* spp. and *Linognathus* spp (e.g. *Bovicola ovis*).

The terms "treating" or "treat" or "treatment" are intended to mean the application or administration of a composition of the invention to an animal that has a parasitic, especially ectoparasitic infestation for the eradication of the parasite or the reduction of the number of the parasites infesting the animal undergoing treatment. It is noted that the compositions of the invention may be used to prevent such a parasitic (re)infestation.

The compositions of the invention are administered in (parasiticidally) effective amounts which are suitable to control the parasite in question to the desired extent.

By "effective amount" is intended a sufficient amount of a composition of the invention to eradicate the infestation of a host animal or reduce the number of parasites infesting the animal. In some embodiments, an effective amount of the active agent achieves at least 70% efficacy against the target parasite.

The efficacy is calculated by methods known in the art, e.g. as outlined in the WAAVP guidelines for the evaluation of ectoparasites. In other embodiments, an effective amount of the active agent achieves at least 80%, or at least 90% efficacy against the target pests. Preferably, an effective amount of the active agent will achieve at least 95%, at least 98% or 100% efficacy against the target parasites.

In each aspect of the invention, the compounds and compositions of the invention can be used to control infestations by a single parasite species or in animals that carry a combination of different parasite species.

The compositions of the invention may be administered continuously, for treatment or prevention of parasitic infections or infestations. In this manner, the compositions of the invention deliver an effective amount of the active compounds to the animal in need thereof to control the target parasites. For a effective control of parasites, one or more applications of the inventive compositions might be necessary. In one embodiment only one administration is necessary to treat existing parasite infestation and to protect the animal from re-infestation.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite. Preferred is a single dose.

In other embodiments for the treatment of livestock animals such as cattle or sheep, doses of the isoxazoline active agent administered may be about 1 to about 30 mg/kg of body weight. More typically the doses administered will be about 1 to about 20 mg/kg or about 1 to about 15 mg/kg.

Preferably, a dose of the isoxazoline active agent administered to livestock animals will be about 1 to about 10 mg/kg of body weight.

The compositions according to the present invention are particularly useful for ruminants such as cattle, sheep, goat, camels, llamas, especially when they are livestock animals, kept for meat and milk or wool or alternatively as working animals.

In one embodiment the animals are bovine animals such as cattle. The efficacy against parasites such as ticks in cattle is very unexpected because the cattle skin is especially challenging for obtaining effective blood levels of isoxazoline compounds after pour-on or spot-on administration.

In this specification, bovine animals are ruminant mammals of the genus *Bos* and include, but are not limited to, cattle, steers, heifers, cows (lactating and non-lactating), calves, bulls, and also buffalo. Especially preferred are beef cattle, i.e. cattle animals kept for meat. In another embodiment the animals are sheep. In another embodiment the animals are goats.

As used herein and throughout "Long acting" refers to a duration of activity that extends beyond 24 hours, preferably extends beyond a week. Preferably beyond two weeks. The protection of cattle animals from tick infestation is an especially preferred embodiment of the current invention.

What constitutes an 'effective amount' for use in the invention, is the amount, therapeutic dose, or quantity of an isoxazoline compound as described herein, that is required for the complete eradication of the parasites infesting such animal, or for at least a significant reduction of the parasites infesting an animal. Alternatively, this may refer to an amount, dose, or quantity that can effectively control and/or reduce presence of parasites in an animal's housing or its surroundings, e.g. the house, building, farm, fields, etc.

To establish that an effective reduction of infestation of an animal, or an effective control and/or reduction of parasites in the surroundings has occurred, and thus: what constitutes such an effective amount, is readily determined by comparing the parasite numbers either on the animal or in an animal's environment, before and after administering an isoxazoline compound as described herein. Detection can be done by counting of the number of parasites visible on an animal, or by counting parasites using a trap or other detection-device in the surroundings. The difference in numbers from such counts made before and after treatment indicates the efficacy of the dose applied. To make such counts statistically reliable, a certain minimal number of host animals or detection devices will need to be monitored.

The effect of the treatment or prevention for use in the invention with an isoxazoline compound as described herein on a parasite, can e.g. be ovicidal, larvicidal and/or adulticidal or a combination thereof. The effect can manifest itself directly, i.e. killing the parasites either immediately or after some time has elapsed, for example when molting occurs, or by influencing the duration or the number of bites, or the amount of blood or body fluid ingested by the parasite per bite. Alternatively, the effect may be on the number of offspring from the parasites, directly or in subsequent generations, e.g. by reducing the parasites' fertility or oviposition efficiency, such as the size, number or quality of eggs laid; the hatching rate; the viability of the outcome; or the gender ratio of the outcome.

Alternatively, the effect on the economic performance of the animals can be monitored, such as for example a difference in: daily weight gain, feed conversion, or the production of milk.

So, although reductions at—or close to 100% are aimed for, however a reduction in parasite numbers of about 5% may already constitute a significant reduction. This because even such a modest reduction already alleviates certain symptoms for affected animals and may restore the animals to an improved economic production level. Parasite mortality is a preferred indication of efficacy of the treatment. Another effect can be reduction of reproduction of the parasite, i.e. generating less offspring.

In a preferred embodiment, the reduction of infestation on an animal, or the control and/or reduction achieved, regards a reduction in the number of a particular type of parasite by at least 5, 10, 15, 20, 25, 30, 40, 50, 60, 70, 75, 80, 85, 90, 91, 92, 93, 94, 95, 96, 97, 98, 99, or even 100%, in that order of preference.

In one embodiment at least 90% tick efficacy is obtained compared to an untreated control group, using the Abbot formula for calculation of the % control efficacy.

The treatment for use in the invention can be made available during a treatment period to a single animal. More advantageous is the treatment at the same time of a group of animals, or to all animals in a single stable, pen, group, house, or farm.

The 'treatment', and similar terms such as 'treating' or 'treat' as used herein, refer to the administration of an effective amount of an isoxazoline as described for use in the invention to an animal which has an infestation—of more or less severity—with parasites of one or more species.

Protection means that existing infestations of the animals are diminished and reduced and/or new infestations that appear after administration of the composition according to the invention are controlled/diminished/reduced or treated.

The term "(parasitic) infection or infestation" includes conditions associated with or caused by one or more (parasitic) pathogens; said conditions include clinical conditions (parasitoses) and sub-clinical conditions.

Sub-clinical conditions are typically conditions not directly leading to clinical symptoms in the parasite infected animal but leading to economic losses. Such economic losses can be e.g. by depression of growth in young animals, lower feed efficiency, lower weight gain in meat producing animals, lower milk production in ruminants, or lower wool-production in sheep.

The term "parasitoses" relates to clinically manifest pathologic conditions and diseases associated with or caused by an infection by one or more parasites, such as, for example parasitic gastroenteritis or anemia in ruminants e.g. sheep and goats or colic in horses.

For use in the invention "Protection from Re-infestation" covers the situation where the animal is exposed to a new infestation by the parasite because it either lives in an environment were living parasites are present or is in close contact with parasite infested animals (or humans)—is therefore "at risk to be infested". Re-infestation is a second or subsequent infestation.

This means an animal that is at a certain point (substantially) free from a parasite infestation is infested (again) from external sources. The composition of the invention kills such new emerging parasites before they can establish an infestation of the animal, or alternatively reduce the number of parasites to limit the irritation and damage to the animal by allowing a non-significant number of parasites.

In one embodiment, the composition exhibits long lasting efficacy and provides protection against parasites in livestock animals for at least one month.

In another embodiment, the compositions of the invention exhibit very long lasting efficacy of at least 50% against ticks that for a period of at least 1 month, at least 2 months, at least 3 months, at least 4 months, at least 5 months, or at least 6 months.

In another embodiment, the compositions of the invention exhibit very long lasting efficacy of at least 70% against ticks that for a period of at least 1 month, at least 2 months, at least 3 months, at least 4 months, at least 5 months, or at least 6 months.

In another embodiment, the compositions of the invention exhibit very long lasting efficacy of at least 90% against ticks that for a period of at least 1 month, at least 2 months, at least 3 months, at least 4 months, at least 5 months, or at least 6 months.

In another embodiment, the compositions of the invention exhibit very long lasting efficacy of at least 50% against lice that for a period of at least 1 month, at least 2 months, at least 3 months, at least 4 months, at least 5 months, or at least 6 months.

In another embodiment, the compositions of the invention exhibit very long lasting efficacy of at least 70% against lice that for a period of at least 1 month, at least 2 months, at least 3 months, at least 4 months, at least 5 months, or at least 6 months.

In another embodiment, the compositions of the invention exhibit very long lasting efficacy of at least 90% against lice that for a period of at least 1 month, at least 2 months, at least 3 months, at least 4 months, at least 5 months, or at least 6 months.

In another embodiment, the compositions of the invention exhibit very long lasting efficacy of at least 50% against mites that for a period of at least 1 month, at least 2 months, at least 3 months, at least 4 months, at least 5 months, or at least 6 months.

In another embodiment, the compositions of the invention exhibit very long lasting efficacy of at least 70% against mites that for a period of at least 1 month, at least 2 months, at least 3 months, at least 4 months, at least 5 months, or at least 6 months.

In another embodiment, the compositions of the invention exhibit very long lasting efficacy of at least 90% against mites that for a period of at least 1 month, at least 2 months, at least 3 months, at least 4 months, at least 5 months, or at least 6 months.

In another embodiment the composition exhibits long lasting efficacy of at least 50% against ticks, mites or lice for a period of at least 6 weeks.

In another embodiment the composition exhibits long lasting efficacy of at least 70% against ticks, mites or lice for a period of at least 6 weeks.

In another embodiment the composition exhibits long lasting efficacy of at least 90% against ticks, mites or lice for a period of at least 6 weeks.

Therefore, one embodiment of the invention is a method wherein the composition according to the invention is administered every month.

Therefore, in another embodiment of the invention the composition according to the invention is administered every six weeks.

Therefore, in another embodiment of the invention the composition according to the invention is administered every 2 months.

Therefore, in another embodiment of the invention the composition according to the invention is administered every 3 months.

In a preferred embodiment of the invention the composition according to the invention is administered as a single treatment per season.

It was surprisingly found that the topical compositions of the invention comprising an isoxazoline active agent provide excellent efficacy against ticks at unexpectedly very low plasma concentrations. In some embodiments, the topical compositions of the invention comprising selected solvents and excipients result in constant low levels of the active agent over a prolonged period of time.

In some embodiments, the concentration of the active agent in the plasma that is sufficient to obtain at least 90% efficacy against ticks is less than or equal to about 200 ng/ml or less than or equal to about 150 ng/ml. In other preferred embodiments, the concentration of the isoxazoline active agent in the plasma required to attain 90% efficacy against ticks is less than or equal to about 100 ng/mL, less than or equal to about 75 ng/mL or even less than or equal to about 50 ng/ml. In other embodiments of the invention, the concentration of the isoxazoline active agent in the plasma required to attain 90% efficacy against ticks is about 75-100 ng/mL, about 50-75 ng/mL or about 30-50 ng/ml.

In one embodiment an effective dose of the composition protects cattle or sheep animals from infestation or re-infestation by ticks, mites, lice and/or biting flies for at least 21 days.

Therefore, in another embodiment of the invention the pour-on composition is administered every 3 weeks or 21 days.

Although not wanting to be bound by theory, the lower plasma concentration required to achieve 90% efficacy from the topical compositions of the invention may indicate that the compositions provide protection against ectoparasites by acting both on the surface of the animal and systemically.

The improved efficacy of the topical compositions of the invention against these tick species at significantly lower plasma concentrations may allow for a longer duration of efficacy based on the ability of the non-active excipients in the inventive compositions to provide a slow delivery of effective amounts of isoxazoline active agents into the blood stream from the site of application.

In another embodiment of the invention, it was surprisingly discovered that the topical compositions of the invention provide 90% efficacy as early as 4 days after administration of the topical composition and also provide long lasting efficacy. In yet other embodiments of the invention, the topical compositions provide efficacy as early as 3 days or 2 days or 1 day after administration.

The fast acting and long lasting protection provided by the compositions of the current invention are unexpected.

In another aspect of the invention, a kit for the treatment or prevention of a parasitic infestation in an animal is provided, which comprises at least one isoxazoline active agent together with a pharmaceutically acceptable carrier and a dispensing device for pour-on application of the composition.

The volume of the topical composition as a spot-on or pour-on applied should be practical and shown to be safe and effective. Typically, the volume applied depends on the size and weight of the animal as well as the concentration of active. It is preferred to apply a volume that allows accurate dosing but does not result in run-off of the composition, especially if the animal moves.

The composition according to the invention allows for a very high concentration of the isooxazoline compound in the composition and therefore allows for a low application volume.

For the pour-on form of the composition, the volume applied can be of the order of about 0.3 to about 100 ml. In other embodiments, volume applied of the pour-on compositions may be about 1 ml to about 100 ml or about 1 ml to about 50 ml. In still other embodiments, the volume may be about 5 ml to about 50 ml or about 10 ml to about 100 ml.

The topical localized spot on composition is applied as a low volume of about 0.01 to 1 ml per kg, preferably about 0.05 to 0.1 ml per kg, with a total volume from 0.3 to 100 ml per animal, preferably limited to a maximum of about 50 ml depending on the target species.

In one embodiment the application volume is 1 ml of the composition per 10 kg of the animal bodyweight, resulting in a total application volume of 50 ml for a 500 kg cattle animal or 8 ml for a 80 kg sheep. These application volumes are convenient for the animal care taker.

In another embodiment the application volume is 1 ml of the composition per 20 kg of the animal bodyweight resulting in a total application volume of 25 ml for a 500 kg cattle animal or 4 ml for a 80 kg sheep.

The pour-on or spot-on compositions according to the invention may be applied using any means known per se, e.g. using an applicator gun or a metering flask, pipette, syringes, roll on, droppers, capsules, foil packages, vials, twist tip containers, metered-dose aerosols or sprays and other single dose and multi-dose containers.

In one embodiment, the compositions of the present invention is administered in a press in bottle insert application device (PIBA) to an animal in need thereof. Such a device allows a health care professional to easily dispense liquids from stock bottles into (oral) syringes.

In administering the composition, the professional opens the bottle and presses the plastic adapter into the opening of the bottle and then attaches the oral syringe to the port of the adapter. Next, the professional may withdraw the dose of medication from the bottle and administer the dose. Then the cap can be replaced on the bottle to be used later.

Presently, animal pour-on products generally require administering larger volumes of a composition, thus, the above-described method of administration is not appropriate. Therefore, present pour-on products are either administered in a dosing gun or a dosing cup. Such methods of administration are less preferred to accurately deliver small volumes of medication.

Thus, the method of administration of the present invention using the PIBA application system allows for more accurate and convenient administration of the presently claimed pour-on liquid preparation.

In one embodiment the current invention is directed to a method of administering the composition according to the invention comprising:
a) Incorporating said composition into a press—in bottle application device; and
b) Administering an effective amount of said composition to an animal in need thereof by pour-on administration on the back of the animal.

This method comprises the following steps: Determine the animal's body weight and select the correct dose using the bottle's dosing chamber, which is calibrated in kilograms of body weight. Hold the bottle upright and at eye level while slowly and gently squeezing the bottle to fill the dosing chamber to the selected mark. Pour the measured volume on the midline of the animal's back extending from the withers to tail head.

An aspect of the invention is to provide a multiple-use container comprising a topical pour-on composition of the invention, from which accurate single dose aliquots of the long lasting topical compositions may be administered.

The composition must remain stable with repetitive exposure to the outside environment, particularly oxygen and water. This embodiment may be particularly useful with the very long lasting compositions of the invention that require administration to an animal infrequently, such as once every 1-6 months, or similar.

Thus, composition stability is particularly important for the multi-dose container application, where the compositions can be exposed to oxygen and water during multiple rounds of opening and closing.

The compositions according to the invention are stable, this means that the active ingredient does not substantially degrade, upon storage in unopened condition and during multiple rounds of opening and closing of the container.

The pour-on composition can also be applied to the animal by other conventional methods, including wiping an impregnated material over at least a small area of the animal, or applying it using a commercially available applicator, by means of a syringe, by spraying or by using a spray race.

Definitions

Terms used herein will have their customary meaning in the art unless specified otherwise.

In this disclosure and in the claims, terms such as "comprises," "comprising," "containing" and "having" and the like can mean "includes," "including," and the like; "consisting essentially of or "consists essentially" likewise is open-ended, allowing for the presence of more than that which is recited so long as basic or novel characteristics of that which is recited is not changed by the presence of more than that which is recited, but excludes prior art embodiments.

As used in the specification and claims, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study, and can be readily appreciated by one of ordinary skill in the art.

In accordance with this detailed description, the following abbreviations and definitions apply. It must be noted that as used herein, the singular forms "a," "an," and "the" include plural referents unless the context clearly dictates otherwise.

The publications discussed herein are provided solely for their disclosure. Nothing herein is to be construed as an admission regarding antedating the publications. Further, the dates of publication provided may be different from the actual publication dates, which may need to be independently confirmed.

Where a range of values is provided, it is understood that each intervening value is encompassed. The upper and lower limits of these smaller ranges may independently be included in the smaller, subject to any specifically-excluded limit in the stated range. Where the stated range includes one or both of the limits, ranges excluding either both of those included limits are also included in the invention. Also contemplated are any values that fall within the cited ranges.

Concentration ranges for the components of the disclosed compositions are expressed as % weight per volume of the final composition unless otherwise stated.

EXAMPLES

The invention is further described by the following non-limiting examples which further illustrate the invention, and are not intended, nor should they be interpreted to, limit the scope of the invention.

As a non-limiting example, the isoxazoline compound fluralaner (Compound A), was investigated for topical delivery to livestock animals such as cattle. In some composition the composition comprises Compound A (fluralaner) and eprinomectin.

Compositions were prepared and evaluated for effectiveness to control ectoparasites such as ticks, in cattle.

TABLE 3

Formulation Examples

| Ingredient | 72 | 73 | 123 | 124 | 37 | 76 | 77 | 14-082 | 14-086 |
|---|---|---|---|---|---|---|---|---|---|
| Compound A | 5.0 | 5.0 | 2.0 | 3.0 | 3.0 | 5.0 | 5.0 | 3.0 | 3.0 |
| Eprinomectin | — | — | — | — | 0.5 | 0.5 | 0.5 | — | 0.5 |
| Eucalyptol | 10.0 | — | — | — | — | 10.0 | — | — | — |
| L-menthol | 10.0 | 10.0 | 10.0 | 10.0 | 10.0 | 10.0 | 10.0 | 10.0 | 10.0 |
| Miglyol 840 | — | 10.0 | 10.0 | 10.0 | 10.0 | — | 10.0 | 10.0 | 10.0 |
| 2-pyrrolidone | 5.0 | 35.0 | 35.0 | 35.0 | 35.0 | 5.0 | 35.0 | 35.0 | 35.0 |
| Isopropyl alcohol | QS | QS | QS | QS | QS | QS | QS | QS | QS |
| BHT | — | — | — | — | 0.5 | 0.5 | 0.5 | — | 0.5 |

TABLE 3a

Cattle spot-on formulation

| Component | 5006294-0005 | 5006294-0006 |
|---|---|---|
| | mg/ml | |
| Fluralaner | 250 | 500 |
| L-menthol | 100 | 100 |
| n-methyl-2-pyrrolidone | 650 | 400 |

TABLE 3b

Sheep spot-on formulation

| Component | 5006294-0002 | 5006294-0003 |
|---|---|---|
| | mg/ml | |
| Fluralaner | 25 | 50 |
| n-methyl-2-pyrrolidone | 300 | 300 |
| Dipropylene glycol monoethyl ether | ca 700 | ca 700 |

In order to prepare the compositions of the Example, the vehicle(s) or a portion of the vehicle(s), are added to the compounding vessel, followed by the remaining excipients and the actives. The combination is mixed until all solids are dissolved. Although not included herein, additives, such as those mentioned in the detailed description, are also included in the vessel and mixed into the composition. The order of addition was not critical.

Biological Example 1

Efficacy Against *Rhipicephalus microplus* Ticks

The efficacy of two pour-on compositions of the invention comprising Compound A were tested against infestations of *Rhipicephalus microplus* ticks compared with two alternative pour-on compositions and an untreated control.

Five healthy head of cattle of 6 to 15 months of age weighing between 70 to 150 kg were used in each study group. Cattle in Group 1 were untreated (control). Cattle in Group 2 were treated on Day 0 with a pour-on composition comprising Compound A in an oily solution at a concentration of 5% (w/v) at a dose of 5 mg/kg; cattle in Group 3 were treated on Day 0 with a pour-on composition comprising Compound A at a concentration of 5% (w/v) in volatile solution I (Pour-on 2 composition see table 1) at a dose of 5 mg/kg; cattle in Group 4 were treated on Day 0 with a pour-on composition comprising Compound A at a concentration of 5% (w/v) volatile solution II (Pour on 3 composition see table 1) at a dose of 5 mg/kg; and cattle in Group 5 were treated on Day 0 with a pour-on composition comprising Compound A at a concentration of 5% (w/v) oily solution at a dose of 5 mg/kg.

The details of the tested Investigational Products are provided in Table 4:

| No % w/v | Fluralaner | BHT | 2-pyrrolidone | L-menthol | Eucalyptol | Kollidon HS-15 | propylene glycol dicaprylocaprate | isopropyl alcohol |
|---|---|---|---|---|---|---|---|---|
| 71-T1 | 5 | NA | 10.0 | 20.0 | NA | NA | QS (ca 60%) | NA |
| 72-T2 | 5 | NA | 5.0 | 10.0 | 10.0 | NA | NA | QS (ca 55%) |
| 73-T3 | 5 | NA | 35.0 | 10.0 | NA | NA | 10.0 | QS (ca 33%) |
| 74-T4 | 5 | NA | NA | 10.0 | NA | 10.0 | QS (ca 69%) | NA |

From Day −28 until Day −1 before treatment, cattle are infested three times a week with approximately 3000 *Rhipicephalus microplus* larvae to establish ongoing infestations. Cattle in Groups 2, 3, 4 and 5 were treated with the respective compositions on Day 0 by measuring the required amount of the solution into a marked disposable syringe and applying the material evenly along the mid-line of the back of each animal from the withers to the tail head.

After treatment each animal was challenged by infestation with approximately 3000 *R. microplus* larvae 3 times a week. For Group 1 (untreated control group) the infestation was continued for two weeks after treatment.

Starting one day after treatment (Day 1), fully engorged female ticks falling from each animal were collected, counted and recorded daily for the duration of the animal phase. Tick collection of the control group (C1) ended after the therapeutic efficacy period due to the fact that the animals will only be re-infested for two weeks after treatment.

In addition, the ticks collected were weighed as a group to measure the impact of the treatment on the weight gain of the ticks compared to the control to assess the vitality and reproductive capability of the treated ticks.

Efficacy of the IVP was determined using the standard ADEQ analysis method as described in Holdsworth, P. A., Kemp, D., Green, P., Peter, R. J., De Bruin, C., Jonsson, N. N., Rehbein, S., Vercruysse, J. World Association for the Advancement of Veterinary Parasitology (W.A.A.V.P.) guidelines for evaluating the efficacy of acaricides against ticks (Ixodidae) on ruminants. Veterinary Parasitology, 136 (2006) 29-43.

To determine the Compound A (fluralaner) plasma pharmacokinetic profile in cattle, blood samples of all treatment groups was collected before treatment and 1, 2, 5, 7, 9, 12, 14, 16, and 21 days after treatment. Thereafter blood samples will be taken weekly (i.e. every 6-8 days) until the end of the animal phase.

FIGS. 1 and 2 show the total tick count % efficacy of the pour-on compositions against *R. microplus* through 115 days post treatment compared with an untreated control group.

Therapeutic daily tick control efficacy (>95%) was reached 3 days after treatment by Group T1, 10 days after treatment by Group T2, 4 days after treatment by Group T3 and 3 days after treatment for Group T4.

Group T1 (5 mg fluralaner/kg body weight), persistent daily tick control efficacy (>95%) fluctuated 3 to 76 days after treatment. The highest efficacy (100%) was maintained from 9 to 55 days after treatment with the lowest efficacy (90.6) recorded 90 days after treatment. Group T1 was removed on Day 98.

Group T2 (5 mg fluralaner/kg body weight), persistent daily tick control efficacy (>95%) fluctuated 23 to 108 days after treatment. The highest efficacy (100%) was maintained from 35 to 42 days after treatment with the lowest efficacy (88.54) recorded 111 days after treatment. Group T2 was removed on Day 117.

Group T3 (5 mg fluralaner/kg body weight), persistent daily tick control efficacy (>95%) fluctuated 4 to 104 days after treatment. The highest efficacy (100%) was maintained from 10 to 15 and 33 to 42 days after treatment with the lowest efficacy (65.27) recorded 110 days after treatment. Group T3 was removed on Day 117.

Group T4 (5 mg fluralaner/kg body weight), persistent daily tick control efficacy (>95%) fluctuated 3 to 72 days after treatment. The highest efficacy (100%) was maintained from 12 to 42 days after treatment with the lowest efficacy (65.25) recorded 77 days after treatment. Group T4 was removed on Day 84.

As shown in the FIGS. 1 and 2, the pour-on compositions of the invention provide excellent efficacy against *Rhipicephalus microplus* ticks for an extended period of time.

The long lasting efficacy above 90% for pour-on composition against *Rhipicephalus microplus* ticks is remarkable compared with pour-on compositions known in the art.

Individual pharmacokinetic parameters of the compositions according to the invention (i.e. $C_{max}$ and AUC) are shown below in Table 5. FIG. 3 summarizes the pharmacokinetic and efficacy results of this study in one graph.

| Parameters (unit) | | Group | | | |
|---|---|---|---|---|---|
| | | 1 | 2 | 3 | 4 |
| $C_{max}$ (ng/mL) | Mean ± SD | 10.7 ± 8.43 | 6.3 ± 6.63 | 11.5 ± 8.19 | 24.6 ± 9.98 |
| $T_{max}$ (days) | Median (range) | 5 (1-7) | 1 (1-77) | 14 (1-69) | 7 (5-9) |
| $AUC_{last}$ (ng.day/mL) | Mean ± SD | 153 ± 59.3 | 95 ± 32.8 | 221 ± 149.0 | 307 ± 145.8 |
| $MRT_{last}$ (days) | Mean ± SD | 22.7 ± 4.08 | 33.5 ± 13.13 | 34.9 ± 15.09 | 12.4 ± 2.38 |

Biological Example 2

Efficacy of Pour-on Composition Against *Haematobia irritans Exiqua* in Cattle.

A paddock pen study was conducted on a commercial farm near Topaz in North Queensland, Australia. The objective of the study was to determine the therapeutic and residual efficacy of four experimental fluralaner pour on formulations against a natural population of buffalo fly (*Haematobia irritans exiqua*) in cattle. The study animals were commercial cattle that remained on farm during the course of the study and had no macrocyclic lactone, organophosphate, synthetic pyrethroid or insect growth regulator external treatment within the previous 3 months. Treatment group details are presented below:

The animals were drafted into their groups on Day 0. The Untreated Group animals were moved to their own separate paddock before treatment commenced. Treatment Groups 2 to 5 were kept separately in small pens in the yards after drafting until they were brought into the race for treatment. Groups 3 and 5 (IVP2 and IVP 4 are compositions according to the invention (see Table 1 No 14-82 and 14-86). Groups 1 and 4 (IVP 1 and IVP 3) were comparative pour-on formulations. Details of the composition are in the following table 6:

| Composition % w/v | IVP 1 14-080 | IVP 2 14-082 | IVP 3 14-084 | IVP 4 14-086 |
|---|---|---|---|---|
| Fluralaner | 3.0 | 3.0 | 3.0 | 3.0 |
| Eprinomectin | — | — | 0.5 | 0.5 |
| 2 pyrrolidone | 35.0 | 35.0 | 35.0 | 35.0 |
| L menthol | 10.0 | 10.0 | 10.0 | 10.0 |

-continued

| Composition % w/v | IVP 1 14-080 | IVP 2 14-082 | IVP 3 14-084 | IVP 4 14-086 |
|---|---|---|---|---|
| Miglyol 840 | 10.0 | 10.0 | 10.0 | 10.0 |
| isopropylalcohol | — | QS | — | QS |
| Glyceryl monocaprylate | QS | — | QS | — |
| BHT | — | — | 0.5 | 0.5 |

Each animal was restrained in ahead crush during treatment application. The animals were treated according to their individual bodyweights recorded prior to treatment on Day −1. The treatments were administered via a 20 mL plastic syringe topically on the back line of the animal, starting approximately 10 cm in front of the shoulder blade and ending at the base of the tail.

Each assessment consisted of counting the number of flies on one whole side of each of all the animals in each separate group. Buffalo fly counts were conducted on Day −6 and Day −1 to determine treatment allocation. Following application of treatments (at Day 0), fly counts were conducted at 1, 3, 7, 14, 21, 28 and 35 days after treatment.

The pre-treatment group buffalo fly counts were uniform between groups and provided an adequate challenge. The counts ranged from an arithmetic mean of 208.3 to 239.2 flies for the five treatment groups. The mean number of buffalo flies per animal remained relatively constant on the untreated control cattle for the first 3 days post treatment ranging from a mean of 233.3 flies to 278.3. Between Days 21 and 35 post treatment the fly numbers increased to a mean of 526.7.

The counts demonstrated that the fly challenge on the farm was adequate during the study.

On Day 1 post-treatment all four IVP groups had mean fly counts significantly lower than the untreated control group.

IVP 2, Group 3 had statistically higher counts than the other treated groups; however control was still relatively high at 82.6% efficacy. The remaining IVPs achieved efficacies >97.7% on Day 1.

Group 4 treated with IVP 3 Fluralaner plus Eprinomectin Pour On—IVP 3 achieved 100% control at Day 3 and 14; however there was no statistical difference in the mean number of flies between Groups 4, 2 and 3 at these assessment times. Efficacy for Group 4 was >99.0% until Day 21. On Days 28 and 35 a moderate level of efficacy was still apparent with 93.3% and 80.9% control respectively.

The remaining formulations maintained high efficacy levels >93.9% until Day 21. All formulations declined on Days 28 and 35 to moderate efficacy levels. At Day 35 cattle treated with all formulations had significantly lower arithmetic mean fly counts than the UTC group.

There was no difference between the IVP groups which ranged from 76.3% efficacy for Group 5 and 80.9% efficacy for Group 4.

The IVP formulations provided a high level of efficacy against the natural buffalo fly populations when administered as a pour on treatment.

The invention is further described by the following numbered paragraphs

1. A liquid veterinary composition for use in the protection and treatment of parasite infestations of animal comprising an effective amount of at least one isoxazoline compound of formula (1)

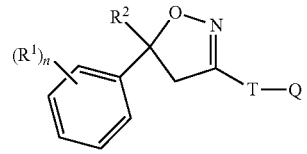

(Formula I)

wherein
$R^1$=halogen, $CF_3$, $OCF_3$, or CN;
n=integer from 0 up to and including 3;
m=1 or 2;
$R^2$=$C_1$-$C_3$ haloalkyl;
T=ring structure: 5-, or 6-membered, or bicyclic, which is optionally substituted by one or more radicals Y;
Y=methyl, halomethyl, halogen, CN, $NO_2$, $NH_2$—C=S, or two adjacent radicals Y together form a chain;
Q=X—$NR^3R^4$, $NR^5$—$NR^6$—X—$R^3$, X—$R^3$, or a 5-membered N-heteroaryl ring, which is optionally substituted by one or more radicals;
X=$CH_2$, $CH(CH_3)$, $CH(CN)$, CO, CS;
$R^3$=hydrogen, methyl, haloethyl, halopropyl, halobutyl, methoxymethyl, methoxyethyl, halomethoxymethyl, ethoxymethyl, haloethoxymethyl, propoxymethyl, thylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)carbonylmethyl, propylaminocarbonylmethyl, cyclopropylaminocarbonylmethyl, propenylaminocarbonylmethyl, haloethylaminocarbonylcyclopropyl, alkylsulfanylalkyl, alkylsulfinylalkyl, alkylsulfonylalkyl, cycloalkyl,

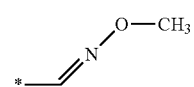

$R^3$-1

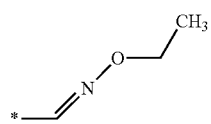

$R^3$-2

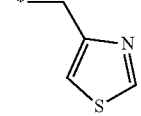

$R^3$-3

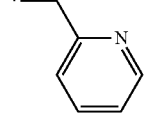

$R^3$-4

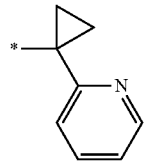

$R^3$-5

R³-6 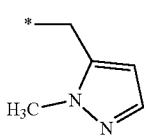

R³-7 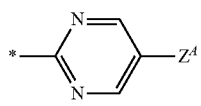

R³-8 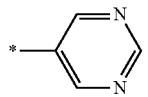

R³-9 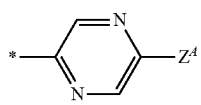

R³-10 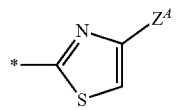

R³-11 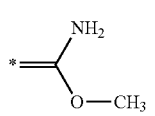

R³-12 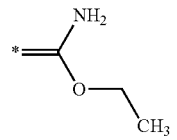

R³-13 

R³-14 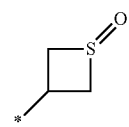

R³-15 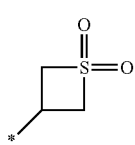

R³-16 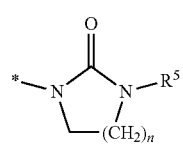

R³-17 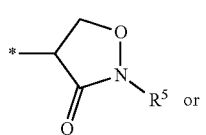 or

R³-18 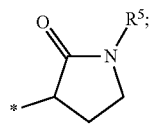

wherein $Z^A$=hydrogen, halogen, cyano, or halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

$R^5$=H, alkyl, or haloalkyl;

$R^6$=H, alkyl, or haloalkyl;

or wherein $R^3$ and $R^4$ together form a substituent selected from the group consisting of:

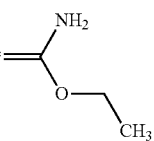 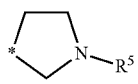 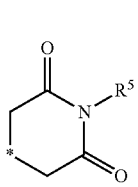

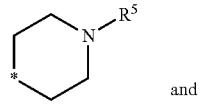  and or a pharmaceutically acceptable salt thereof, wherein the composition is administered as a pour on and comprises a pharmaceutically acceptable carrier comprising at least one dermal penetration enhancer and a solvent system, wherein the dermal penetration enhancer comprises menthol, and the solvent system comprises a pyrrolidone solvent.

2. The liquid veterinary composition of paragraph 1, wherein T is selected from

T-1 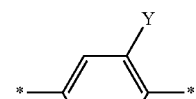

T-2 

T-3 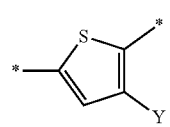

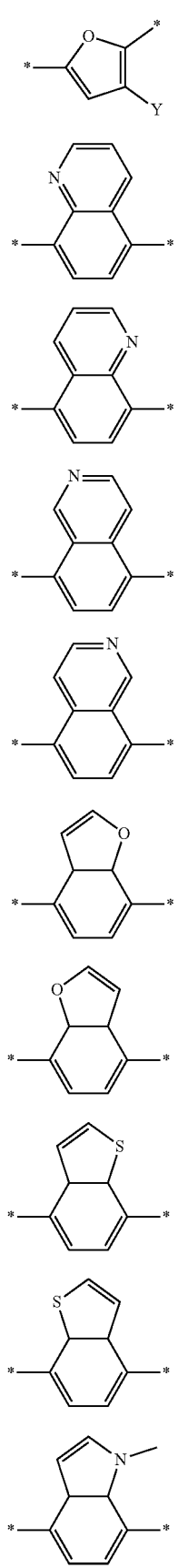
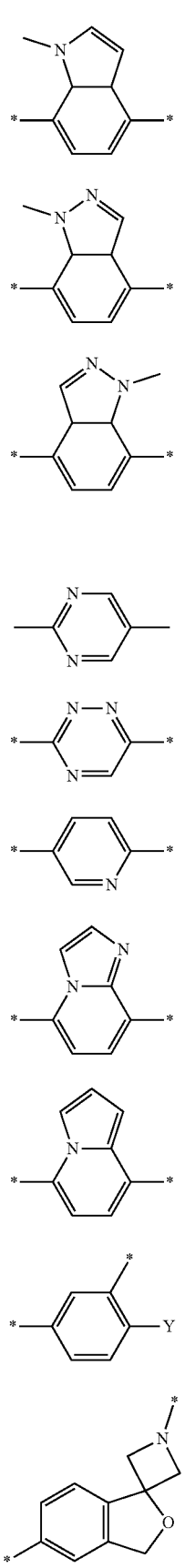

T-24
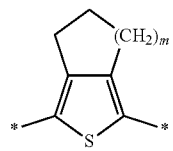
T-25
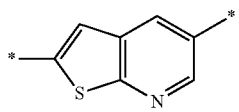
wherein in T-1, T-3 and T-4, the radical Y=hydrogen, halogen, methyl, halomethyl, ethyl, or haloethyl and wherein Q is selected from
Q-1
*—X—N(R³)(R⁴)
Q-2
Q-3
Q-4
Q-5
Q-6
Q-7
Q-8
Q-9
wherein $R^3$, $R^4$, X and $Z^A$ are as defined above, and
$Z^B =$
$Z^B$-1
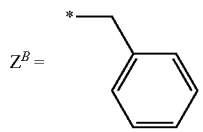
$Z^B$-2
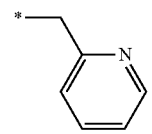
$Z^B$-3
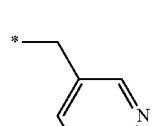
$Z^B$-4
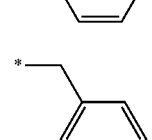
$Z^B$-5
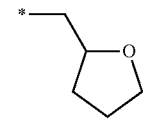
$Z^B$-6
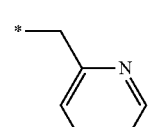
$Z^B$-7
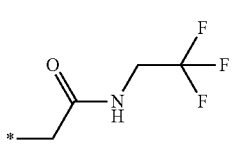
$Z^B$-8
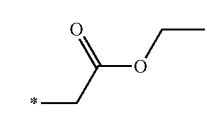
$Z^B$-9
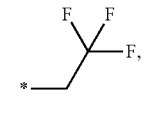
$Z^D =$
$Z^D$-1
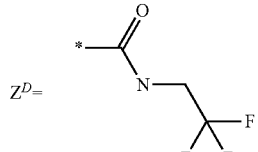
$Z^D$-2
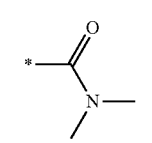

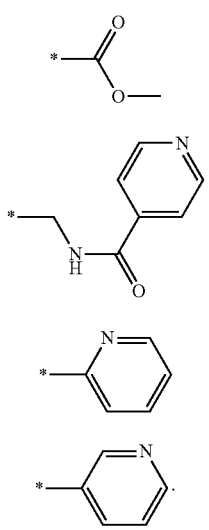

3. The liquid veterinary composition of paragraphs 1 or 2, wherein the solvent system comprises a volatile solvent.
4. The liquid veterinary composition of paragraphs 1 or 2, wherein the composition comprises about 2 to about 20% w/v of the volatile solvent.
5. The liquid veterinary composition of any of paragraphs 1 to 3, wherein the volatile solvent is an alcohol solvent.
6. The liquid veterinary composition of any of paragraphs 1 to 4, wherein the composition comprises about 5 to about 60% w/v of the alcohol solvent.
7. The liquid veterinary composition of any of paragraphs 1 to 5, wherein the alcohol solvent is isopropyl alcohol.
8. The liquid veterinary composition of paragraphs 1 or 2, wherein the composition comprises a glycerol ester.
9. The liquid veterinary composition of paragraphs 1 or 2, wherein the glycerol ester is selected from saturated or unsaturated fatty acid mono- and di-esters of propylene glycol or mono-, di- and tri-esters of glycerol with alkyl chain lengths from $C_8$-$C_{14}$, saturated fatty acids with alkyl chain lengths from $C_8$-$C_{14}$, unsaturated fatty acids with alkyl chain lengths from $C_{14}$-$C_{22}$, saturated fatty alcohols with alkyl chain lengths from $C_8$-$C_{14}$, and unsaturated fatty alcohols with alkyl chain lengths from $C_{14}$-$C_{22}$ or mixtures thereof.
10. The liquid veterinary composition of paragraph 8, wherein the glycerol ester is selected from the group consisting of propylene glycol dicapryocaprate, glyceryl monocaprylate, and mixtures thereof.
11. The liquid veterinary composition of any of paragraphs 8 to 10, wherein the composition comprises about 5 to about 70% w/v of the glycerol ester.
12. The liquid veterinary composition of any of paragraphs 8 to 11, wherein the glycerol ester is glyceryl monocaprylate.
13. The liquid veterinary composition any of paragraphs 1 to 12, wherein the isooxazoline compound is fluralaner.
14. The liquid veterinary composition any of paragraphs 1 to 13, wherein the composition comprises from about 1 to about 20% (w/v) of the isoxazoline compound.
15. The liquid veterinary composition any of paragraphs 1 to 14, wherein the composition comprises from about 20 to about 50% (w/v) of the isoxazoline compound.
16. The liquid veterinary composition of any of paragraphs 1 to 15, wherein the composition comprises about 2 to about 20% w/v of menthol.
17. The liquid veterinary composition of any of paragraphs 1 to 16, wherein the pyrrolidone solvent is 2-pyrrolidone, N-methyl-2-pyrrolidone, and/or mixtures thereof.
18. The liquid veterinary composition of any of paragraphs 1 to 17, wherein the composition comprises about 5 to about 50% w/v of the pyrrolidone solvent.
19. The liquid veterinary composition of any of paragraphs 1 to 18, further comprising a propylene glycol dicaprylate/dicaprate.
20. The liquid veterinary composition of any of paragraphs 1 to 19, wherein the composition comprises about 5 to about 80% w/v of the propylene glycol dicaprylate/dicaprate.
21. The liquid veterinary composition of any of paragraphs 1 to 20, wherein the composition comprises about 5 to about 50% w/v of the pyrrolidone solvent and about 5 to about 80% w/v of the propylene glycol dicaprylate/dicaprate.
22. The liquid veterinary composition of 1 to 7, comprising:
    a) from about 0.5% to about 15% w/v of at least one isoxazoline compound;
    b) from about 5% to about 15% w/v of menthol;
    c) from about 10% to about 50% w/v of isopropyl alcohol;
    d) from about 10% to about 40% w/v of a pyrrolidone solvent; and
    e) from about 5% to about 80% w/v of a propylene glycol dicaprylate/dicaprate.
23. The liquid veterinary composition of paragraph 22, wherein the composition comprises about 2 to about 5% of the isoxazoline compound, and the carrier comprises about 10% w/v of menthol, between about 35 and about 55% w/v of isopropyl alcohol, between about 5 and about 35% w/v of 2-pyrrolidone and/or about 10% w/v of propylene glycol dicaprylate/dicaprate.
24. The liquid veterinary composition of any one of paragraphs 1 to 7, wherein the composition comprises about 2, about 3, or about 5% w/v of the isoxazoline compound; and the carrier comprises about 35 or about 55% w/v of isopropyl alcohol and about 5 or about 35% w/v of 2-pyrrolidone.
25. The liquid veterinary composition of paragraph 1 to 7, wherein the composition comprises about 20 to about 50% of the isoxazoline compound, and the carrier comprises about 5 to about 15% of menthol, between about 35 and about 55% w/v of isopropyl alcohol, between about 5 and about 40% w/v of 2-pyrrolidone and/or about 10% to 70% w/v of propylene glycol dicaprylate/dicaprate.
26. The liquid veterinary composition of paragraph 1 to 7, wherein the composition comprises about 2, about 3, or about 5% w/v of the isoxazoline compound; and the carrier comprises about 35 or about 55% w/v of isopropyl alcohol and about 5 or about 35% w/v of 2-pyrrolidone.
27. The liquid veterinary composition of any one of paragraphs 1 to 26, wherein the isoxazoline compound is selected from the group consisting of fluralaner, afoxolaner, lotilaner, and sarolaner.

28. The liquid veterinary composition of any one of paragraphs 1 to 27 for use in the manufacturing of a medicament to control parasites wherein the animal is a cattle or sheep animal.

29. The liquid veterinary composition of any one of paragraphs 1 to 28 wherein the ectoparasite infestation is an infestation by ticks and/or lice.

30. A method of protecting a cattle animal from ectoparasite infestation comprising administering an effective dose of the liquid veterinary composition of any one of paragraphs 1 to 27 to an animal in need thereof.

31. Use of the liquid veterinary composition of any one of paragraphs 1 to 27 in the manufacture of a medicament for the protection of cattle from ectoparasite infestation and/or the treatment of ectoparasite infestation, preferably from tick or lice infestation.

32. Use of the liquid veterinary composition of any one of paragraphs 1 to 27 in the manufacture of a medicament for the protection of sheep from ectoparasite infestation and/or the treatment of ectoparasite infestation, preferably from blowfly strike.

We claim:

1. A liquid cattle pour on composition comprising an effective amount of fluralaner, or a pharmaceutically acceptable salt thereof, wherein the composition is a pour on and comprises
    a) from about 1% to about 10% w/v of fluralaner;
    b) from about 5% to about 15% w/v of menthol;
    c) from about 10% to about 40% w/v of 2-pyrrolidone;
    d) from about 10% to about 50% w/v of a propylene glycol dicaprylate/dicaprate;
    e) optionally from about 0.01% to about 0.5% (w/v) of a colorant; and
    f) isopropyl alcohol, q.s. wherein the concentration of the isopropyl alcohol is from about 20% to about 45% w/v.

2. The liquid cattle pour on composition of claim 1, comprising:
    a) about 5% w/v of fluralaner;
    b) about 10% w/v of menthol;
    c) from about 33% to about 35% w/v of isopropyl alcohol;
    d) about 35% w/v of 2-pyrrolidone; and
    e) about 10% w/v of a propylene glycol dicaprylate/dicaprate.

3. The liquid cattle pour on composition of claim 1, wherein the fluralaner concentration is about 5% w/v.

4. The liquid cattle pour on composition of claim 1, wherein the menthol concentration is about 10% w/v.

5. The liquid cattle pour on composition of claim 1, wherein the 2-pyrrolindone concentration is about 20% w/v.

6. The liquid cattle pour on composition of claim 1, wherein the propylene glycol dicaprylate/dicaprate concentration is about 10% w/v.

7. The liquid cattle pour on composition of claim 1, wherein the colorant is FD&C Blue no 1, FD&C Yellow no 5, Chlorophyllin or mixtures thereof.

8. A method of protecting a cattle animal from ectoparasite infestation comprising administering an effective dose of the liquid cattle pour on composition of claim 1.

9. The method of claim 8, wherein the pour on administration of the liquid cattle pour on composition controls ectoparasite infestation in cattle.

10. The method of claim 8, wherein the pour on administration of the liquid cattle pour on composition controls tick or lice infestation in cattle.

* * * * *